US011817669B2

United States Patent
Alfano et al.

(10) Patent No.: US 11,817,669 B2
(45) Date of Patent: Nov. 14, 2023

(54) TABLE-TOP ULTRA SUPERCONTINUUM AND HIGHER HARMONIC GENERATION SOURCE FOR MICROSCOPY

(71) Applicant: Robert R. Alfano, Bronx, NY (US)

(72) Inventors: Robert R. Alfano, Bronx, NY (US); Shah Faisal B. Mazhar, Bronx, NY (US); Mikhail Sharonov, Lexington, NY (US); Lingyan Shi, San Diego, CA (US)

(73) Assignee: Robert R. Alfano, Bronx, NY (US)

( * ) Notice: Subject to any disclaimer, the term of this patent is extended or adjusted under 35 U.S.C. 154(b) by 0 days.

(21) Appl. No.: 17/532,834

(22) Filed: Nov. 22, 2021

(65) Prior Publication Data

US 2022/0166177 A1 May 26, 2022

Related U.S. Application Data

(60) Provisional application No. 63/116,527, filed on Nov. 20, 2020.

(51) Int. Cl.
*H01S 3/10* (2006.01)
*H01S 3/00* (2006.01)
(Continued)

(52) U.S. Cl.
CPC .......... *H01S 3/0092* (2013.01); *H01S 3/0057* (2013.01); *H01S 3/0085* (2013.01);
(Continued)

(58) Field of Classification Search
CPC .... H01S 3/0092; H01S 3/0057; H01S 3/0085; H01S 3/107; H01S 3/108; H01S 3/1106; H01S 3/1121; H01S 5/0085
See application file for complete search history.

(56) References Cited

U.S. PATENT DOCUMENTS

| | | | |
|---|---|---|---|
| 8,633,437 B2 * | 1/2014 | Dantus | G01N 21/65 |
| | | | 250/281 |
| 2010/0234837 A1 * | 9/2010 | Alfano | G02F 1/3536 |
| | | | 435/284.1 |

(Continued)

*Primary Examiner* — Kinam Park
(74) *Attorney, Agent, or Firm* — Nolte Lackenbach Siegel; Myron Greenspan

(57) ABSTRACT

In this patent, we teach methods to generate coherent X-ray and UUV rays beams for X ray and UUV microscopes using intense femtosecond pulses resulting the Ultra-Supercontinuum (USC) and Higher Harmonic Generation (HHG) from $\chi3$ and $\chi^5$ media produce from electronic and molecular Kerr effect. The response of $n_2$ ($\chi3$) and $n_4$ ($\chi5$) at the optical frequency from instantaneously response of carrier phase of envelope results in odd HHG and spectral broadening about each harmonic on the anti-Stokes side of the pump pulse at wo typically in the visible, NIR, and MIR. From the slower molecular Kerr response on femtosecond to picosecond from orientation and molecular motion on $n_2$ and $n_4$ which follow the envelope of optical field of the laser gives rise to extreme broadening without HHG. The resulting spectra extend on the Stokes side towards the IR, RF to DC covering most of the electromagnetic spectrum. These HHG and Super broadening covering UUV to X rays and possibly to gamma ray regime for microscopes.

22 Claims, 21 Drawing Sheets

(51) Int. Cl.
  *H01S 3/1106* (2023.01)
  *H01S 3/108* (2006.01)
  *H01S 3/107* (2006.01)
  *H01S 5/00* (2006.01)
  *G21K 7/00* (2006.01)
  *A61B 6/00* (2006.01)
  *G02F 1/35* (2006.01)

(52) U.S. Cl.
  CPC .............. *H01S 3/107* (2013.01); *H01S 3/108* (2013.01); *H01S 3/1106* (2013.01); *H01S 3/1121* (2013.01); *H01S 5/0085* (2013.01); *A61B 6/484* (2013.01); *G02F 1/3528* (2021.01); *G21K 7/00* (2013.01); *G21K 2207/005* (2013.01)

(56) References Cited

U.S. PATENT DOCUMENTS

| | | | | |
|---|---|---|---|---|
| 2014/0285876 A1* | 9/2014 | Yoshida | ................ | H01S 5/1085 |
| | | | | 359/341.3 |
| 2016/0238532 A1* | 8/2016 | Freudiger | .............. | G02B 21/16 |
| 2017/0153435 A1* | 6/2017 | Alfano | ................... | G06N 10/00 |
| 2019/0027890 A1* | 1/2019 | Louot | ................... | H01S 3/0092 |
| 2022/0166177 A1* | 5/2022 | Alfano | ................... | H01S 3/108 |
| 2022/0247143 A1* | 8/2022 | Abdolvand | ......... | H01S 3/06704 |

\* cited by examiner

TABLE-TOP ULTRA SUPERCONTINUUM AND HIGHER HARMONIC GENERATION SOURCE FOR MICROSCOPY

BACKGROUND OF THE INVENTION

1. Field of the Invention

The invention generally relates to microscopes and, more specifically, to a table-top ultraviolet x-ray supercontinuum anti-stokes microscope and nir, mir, ir, thz supercontinuum stokes microscope.

2. Background

There is a need to achieve a better resolution and transparency for compact microscope and imaging of bio and condensed matter in a wider spectral range. Coherent X-rays and deep UV (UUV) sources can be used to fill this gap. There is a lack of microscopes in the X-ray, UV, NIR, MIR, IR, and THz spectral zone. The focus of this patent is to fill the electromagnetic spectral void by producing a microscope with Table-Top X-ray and UUV source for deep high-resolution nanometer scale imager and NIR, MIR, IR, and THz for microscale imaging.

Although the research and developmental focus has been changed from Lamp sources to lasers and to use nonlinear optics with ultrafast lasers to create multi-photon effects such as 2 and 3 Photon absorption and emission, second harmonic generation, and Stimulated Raman imaging using picosecond and femtosecond pulses in NIR for deep imaging [1-11]. The limitation of the laser sources spans from the ultra-violet to the IR for well-defined wavelengths. Higher resolution with submicron scale which can further be integrated with STED approaches and STORM approaches use of single photons, there is a need of a new microscope in different spectral zones extending from the X-rays, UUV, UV to THz region for better biomedical imaging.

The USC will be generated in various types of optical media like liquids such as $CS_2$, rare gases (Argon and Krypton), condensed matter such as semiconductors (GaP, InSb, GaN, and Alloys), glass, thin metals, superconductors, nitrogen, and hydrogen extremely using femtosecond laser pulses in the visible and NIR frequencies/wavelengths such as about 517 nm, 530 nm, 800 nm, 1035 nm, and 1064 nm. These wavelengths are denoted by the pump frequency wo in the various plots and theory. These media can be placed into hollow holey photonic bandgap structures and fibers to confine the optical interaction to generate USC.

There are various intense X-ray sources to examine a body part. There are some in comparison to the X-Rays from HHG and USC:
- X-ray tube, a vacuum tube that produces incoherent X-rays when current flows through it hitting electrons a target (incoherent)
- X-ray laser (coherent)
- Synchrotron, which produces X-rays as synchrotron coherent radiation
- Cyclotron, which produces X-rays as cyclotron coherent radiation
- HHG generation by tabletop pumped lasers from ultrafast laser coherent.

The Brilliance of X-ray sources are:
1) Incoherent source:
   a) X-ray tube is $\sim 10^7$ photons/(sec·mm$^2$·mrad$^2$)
2) Coherent source:
   a) Synchrotrons are $10^{18}$-$10^{20}$ photons/(sec·mm$^2$·mrad$^2$)
   b) Typical gas $\sim 6 \times 10^{10}$ photon/sec The purpose of a USC source is to teach the intense Brilliance in the X-ray source. The ultrafast Ultra-SC has a brilliance about $10^{21}$ photons/(sec·mm$^2$·mrad$^2$). The unit of Brilliance B is the number of photons/(sec·mm$^2$·mrad$^2$).

To estimate B for USC source we start with continuum span ΔE span ($\Delta\omega_{max}$).

The USC spans from ~1 eV to 10 GeV=over $10^{10}$ eV assume mostly equal spread in frequency.

The number of photons for Ti-sapphire laser system for 1 mJ pulse energy in 100 fs is $\sim 10^{18}$ photons give, $$N_L = \frac{10^{18} \text{ photons}}{100 \text{ fs}} = 10^{31} \text{ Photons/sec}$$

from laser pulse. The USC spans this energy over $10^{10}$. The number of UV-X-rays is, $$N_{UV-X} = (10^{-10})10^{31} = 10^{21} \text{ photons/sec}.$$

The USC Brilliance is obtained in 1 mm$^2$ area and solid angle (1 mrad)$^2$, $$B_{USC} \sim 10^{21} \text{ photons/(sec·mm}^2\text{·mrad}^2),$$

which is comparable or greater than the X-ray created by conventional large X-ray sources [12]. The USC Brilliance is higher than the counterpart large X-ray sources [See FIG. 1(a)].

BRIEF DESCRIPTION OF THE FIGURES

The above and other aspects, features and advantages of the present invention will be more apparent from the following description when taken in conjunction with the accompanying drawings, in which.

DETAILED DESCRIPTION

Light poses salient properties of coherence, polarization, wave front, and wavelength. James Maxwell in 1845 laid down the foundation using a set of equations to describe Electromagnetic waves. Light acts as a courier transferring information from one point to another, it can act as a chemist or a biologist to alter and probe the matter. The basic equation to describe an electromagnetic wave can be given by the following:

$$E(t)=E_0(t)\hat{e}e^{-i(\omega_L t-kz+\varphi(t))}=E_0(t)\hat{e}\cos(\omega_L t-kz+\varphi(t))) \quad (1)$$

where, the electric field envelope amplitude is $$E_0(t) = E_0 e^{-\frac{t^2}{T^2}},$$

the polarization is ê, the propagation constant is $$k = \frac{n\omega_L}{c},$$

and the pump angular frequency is denoted as $\omega_L=\omega_0$. The carrier envelope phase $\phi(t)$ is given by, $$\phi(t) = \omega_L t - \frac{n\omega_L}{c}z + \varphi(t). \quad (2)$$

Figure 1A:
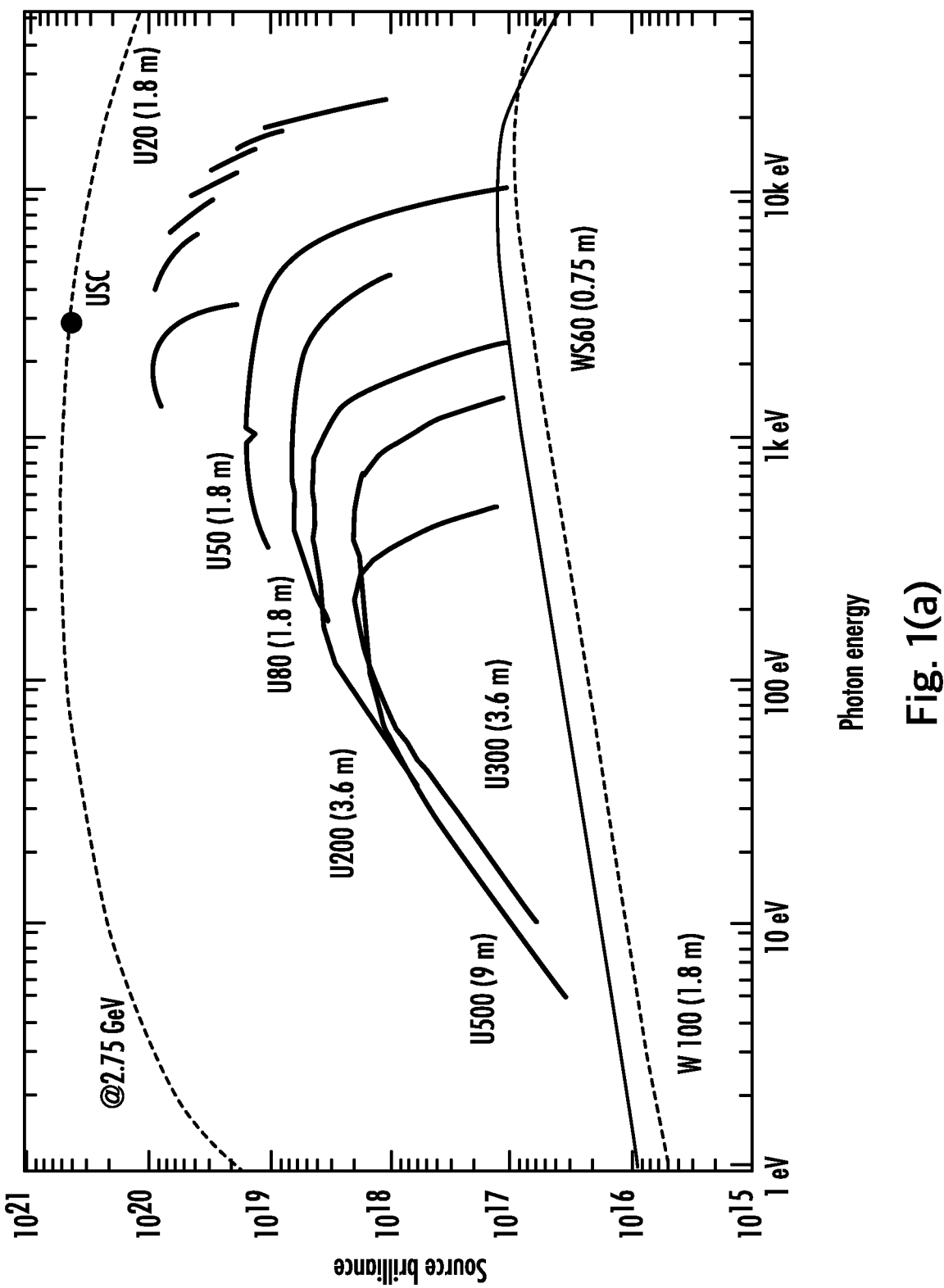
FIG. 1(a) illustrates: Source Brilliance vs. Photon energy of different X-ray sources with the indication of USC X-rays (11) [Dotted curve and the dot for USC is calculated B from USC].
Figure 1B:
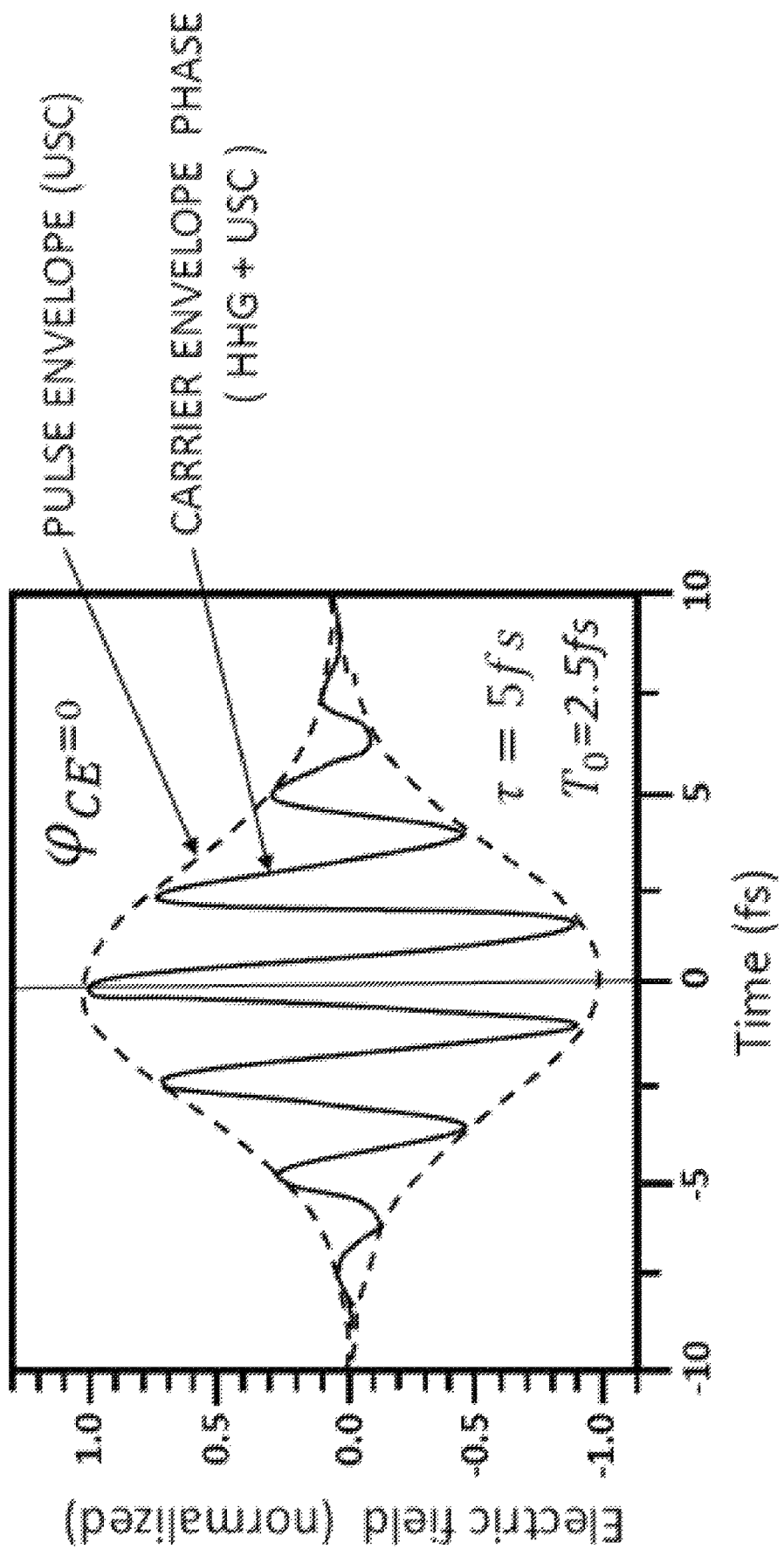
FIG. 1(b) illustrates Electric Field of light pulse from Eq 1.

The light can be modulated in amplitude (Amplitude Modulation, AM) and phase (Frequency Modulation, FM). The electric field E is depicted in FIG. 1b for envelope of bell shape and carrier phase in time. These two relate properties are key in the teachings to give rise to USC from changes of index of refraction from Kerr processes in materials to produce USC from SPM and HHG.

Ever since the light was coherently produced from the laser in 1960 by Maiman at a narrow band of frequency, there has been a search to produce more frequencies by nonlinear optical effects to create new frequencies such as second harmonic generation, stimulated Raman scattering, and four-wave parametric generated by Terhune at Ford Motor Company and by tunable dye and solid-state lasers for the applications in fields such as communication, display, imaging, chemistry, and biology.

Kerr effect started in 1875 using DC effect [1]. In 1956, Buckingham proposed a higher frequency optical Kerr effect when an intense linearly polarized light beam traveling through an optical isotropic medium in the material becomes temporal anisotropic [2]. Buckingham extended Kerr's idea by assuming instantaneous response of the index of Kerr part of the molecules to the applied electric field in terms of the modulating refractive index over time. A major advance occurred when Duguay in 1969 realized this experimentally by extending the traditional DC/AC Kerr and theoretical proposed optical Kerr effect [2] processes into the optical regime where E is the optical field from a 10 ps laser pulse, and it now is called the Optical Kerr Gate.

In the Kerr effect, the material behaves optically as though it were a uniaxial crystal in which the electric field of the laser acts as an optic axis. The major mechanisms responsible for inducing birefringence can arise from distortion of electron clouds, rotations of molecules, and disturbance of molecular motion. The Optical Kerr gate has been used extensively as an ultrafast optical gate.

The linear and nonlinear polarization density is given by:

$$P=\chi^1 E+\chi^2 E^2+\chi^3 E^3+\chi^4 E^4+\chi^5 E^5, \quad (3)$$

where each of the terms of the Eq. 3 represents linear polarization, Second Harmonic Generation (SHG), Third Harmonic Generation (3HG), 4$^{th}$ Harmonic Generation (4$^{TH}$ HG), and 5$^{th}$ Harmonic Generation (5$^{th}$ HG) respectively. For isotropic media such as liquid, gases, glasses, and rare gas atoms: $\chi^2=\chi^4=0$: where $\chi^1 \rightarrow n_0$, $\chi^2 \rightarrow n_1$, $\chi^3 \rightarrow n_2$, $\chi^5 \rightarrow n_4$ for materials.

Alfano and Shapiro in 1970, using 532 nm 5 ps ultrafast laser pulses made a startling observation and discovery of the white light supercontinuum covering the visible and attributed it to SPM and self-focusing on various crystals, liquids, and glasses, including liquefied and solidified rare gases [3-5]. They showed that the electronic mechanism for SPM is important in all materials and dominates all other processes in some materials, e.g., even in rare noble liquid Argon, and liquid and solid Krypton [3]. The Maxwell rainbow goes beyond the visible spectrum into the UV, blue, and red into IR, NIR, MIR spectral zones using various bulk and fiber materials for various applications such as communication, accurate frequency comb clocks, spectroscopy, and biomedical imaging fields.

The electronic distortion mechanism [2-3] arises from quantum transitions is present in all condensed and gases material, a fact consistent with the experimental observation of SPM spectra in all samples studied under intense ultrafast laser excitation.

In this patent, we focus on teaching the ultra-spectral broadening spanning from X-rays, UUV, UV, visible, NIR, to THz from gases and condensed matter from the Kerr nonlinear index of refraction in the slow varying approximation (SVA) arising from $n_2I$ and $n_4I^2$ at extremely high laser pulse intensity $\geq 2\times10^{14}$ W/m$^2$ where $n_2$ arises from slow ps response $\chi 3$ and $n_4$ arise from $\chi^5$ to produce ultra-supercontinuum (USC). While propagating, an intense optical pulse changes the index of refraction by causing the direct distortion of the electronic cloud (instantaneous faster time response) and the molecular motion (average slower time response) depending on pulse duration. The change in index leads to spectral broadening from self-phase modulation (SPM).

At extreme intensities ($\geq 1\times10^{14}$ W/m$^2$), the instantaneous response leads to Higher Harmonic Generation (HHG) and Supercontinuum with respect to each odd harmonic. The average response leads to the super spectral broadening called Ultra-supercontinuum without HHG.

In 1956, Buckingham [2] introduced optical Kerr effect as an analog to DC Kerr gate from the change in refractive index, n from E as, $$n = n_0 + n_2 E^2, \quad (4)$$

The response time of the Kerr effect can be instantaneous following the optical cycles arising from the direct distortion of electronic cloud and from averaging the slower molecular motion which follows the envelope of the optical field. A slower response from other mechanism can alter the index of refraction. Here the key mechanism to give rise to the Ultra spectral broadening occurs from the electronic and molecular fast motions.

The index of refraction n(t) has two forms:
Slow response chooses:

$$\langle n \rangle = n_0 + \frac{1}{2} n_2 [E_0(t)]^2, \quad (5)$$

which causes SPM for slow temporal response to $E_0(t)$, the envelope's temporal shape such as Gaussian and other symmetrical and distorted pulse shapes; and Instantaneous form follows the electric field envelope and optical cycle, $$n(t) = n_0 + n_2 \left[ E_0 e^{-\frac{t^2}{T^2}} \cos\phi(t) \right]^2, \quad (6)$$

which causes ESPM for fast electronic cloud temporal response and molecular redistribution temporal response to E(t).

Based on the response of nonlinear refractive indices response given by Eq. 5 and 6, we teach in TWO PARTS: 1. Envelope SPM producing extreme spectral broadening called the Ultra-supercontinuum (USC); and 2. Carrier phase and envelope which results in Higher Harmonic Generation (HHG).

In part 1, we will teach the spectral broadening caused by the slow response to the envelope at extreme intensities which will include both the first nonlinear index $n_2$ followed by the additional term caused from higher intensity by activating $n_4$.

In part 2, we will discuss (HHG) with spectral broadening caused by the instantaneous response to the phase and the envelope at extreme intensities which will include only the first nonlinear index $n_2$ but can be extended to the higher refractive indices like $n_4$.

One of the highest $n_2$ materials CS$_2$ liquid was selected with its large nonlinear index and fast response time of 1.8 ps as compared to the electronic part to demonstrate the ultra-supercontinuum broadening with an extreme laser beam with $n_2$ and $n_4$. The fastest electronic materials are the rare gas atoms from their spherical shape in the gaseous, liquid, and solid forms to produce supercontinuum and HHG. A faster condensed matter sample are the different glasses such as silica and chalcogenides with the response time in the femtosecond scale and small and large bandgap semiconductors such as AlN, GaN, InSb, InAs, chalcogenides, and alloys. The underlying mechanism of the nonlinear index of refraction can arise from electronic, rotation, libration, and vibration motions. CS$_2$ demonstrates the largest nonlinear index from the rotation mechanism and high index $n_0$. $\chi^5$ arises for dispersion-less semiconductor media in six photon processes. Here in Eq. 4, the change in index n follows the electric field envelope E(t) in time.

In the teachings presented here, the generation of UV and X-ray frequencies arises from the two parts of the Kerr effect: 1. one arising from the slow varying average (SVA) effect of the carrier envelope of the light pulse to produce USC and the other: 2. from the instantaneous electronic response to the optical frequency of the fast-varying part of the optical electric field following the optical cycle to produce HHG and Supercontinuum about the laser frequency (wo) and about each odd harmonic. Liquid and gaseous media can be placed in micrometer scale optical hollow fibers to generate the USC from ESPM, SPM, XPM, Four-wave mixing, and Soliton generation over long interaction length.

Part 1:

In the first part, the spectral broadening is caused by the average index of refraction $\langle n(t) \rangle$ following the envelope of the electric field which includes $n_2$ and $n_4$ to reveal the supercontinuum without HHG.

The average refractive index follows the slow varying envelope including $n_2$ and $n_4$ part where the index of refraction becomes, $$\langle n(t) \rangle = n_0 + n_2 I + n_4 I^2, \quad (7)$$

where $I = E_0(t)^2$ follows the envelope to produce super ultra-broadening. The phase from Eq. 2 becomes, $$\phi(t) = \omega_L t - \frac{(n_0 + n_2 I + n_4 I^2)\omega_L}{c} z, \quad (8)$$

which becomes modulated by its own light intensity I(t) via $n_2$ and $n_4$. The new frequency is, $$\Omega(t) = \frac{d\phi(t)}{dt} = \omega_L - \left( 0 + n_2 \frac{dI}{dt} + n_4 \frac{dI^2}{dt} \right) \frac{\omega_L z}{c}. \quad (9)$$

The outgoing electric field becomes modulated as, $$E(t) = E_0 e^{-\frac{t^2}{T^2}} e^{-i\left(\omega_L - \frac{\langle n(t) \rangle \omega_L}{c} z\right)}. \quad (10)$$

To produce SPM induced spectra via $n_2$ and $n_4$, the Eq. 7 and 8 are used and using Fast Fourier Transform (FFT) of E(t) [into Eq. 10] is transformed to obtain E($\omega$) and power spectra $$S(\omega) = \frac{c}{4\pi} |E(\omega)|^2.$$

The simulated ultra-supercontinuum (USC) and the enhanced version results are shown next for various parameters from intensities from $10^{14}$ to $10^{16}$ W/m², $n_2$, and $n_4$ for $CS_2$.

Figure 1C:
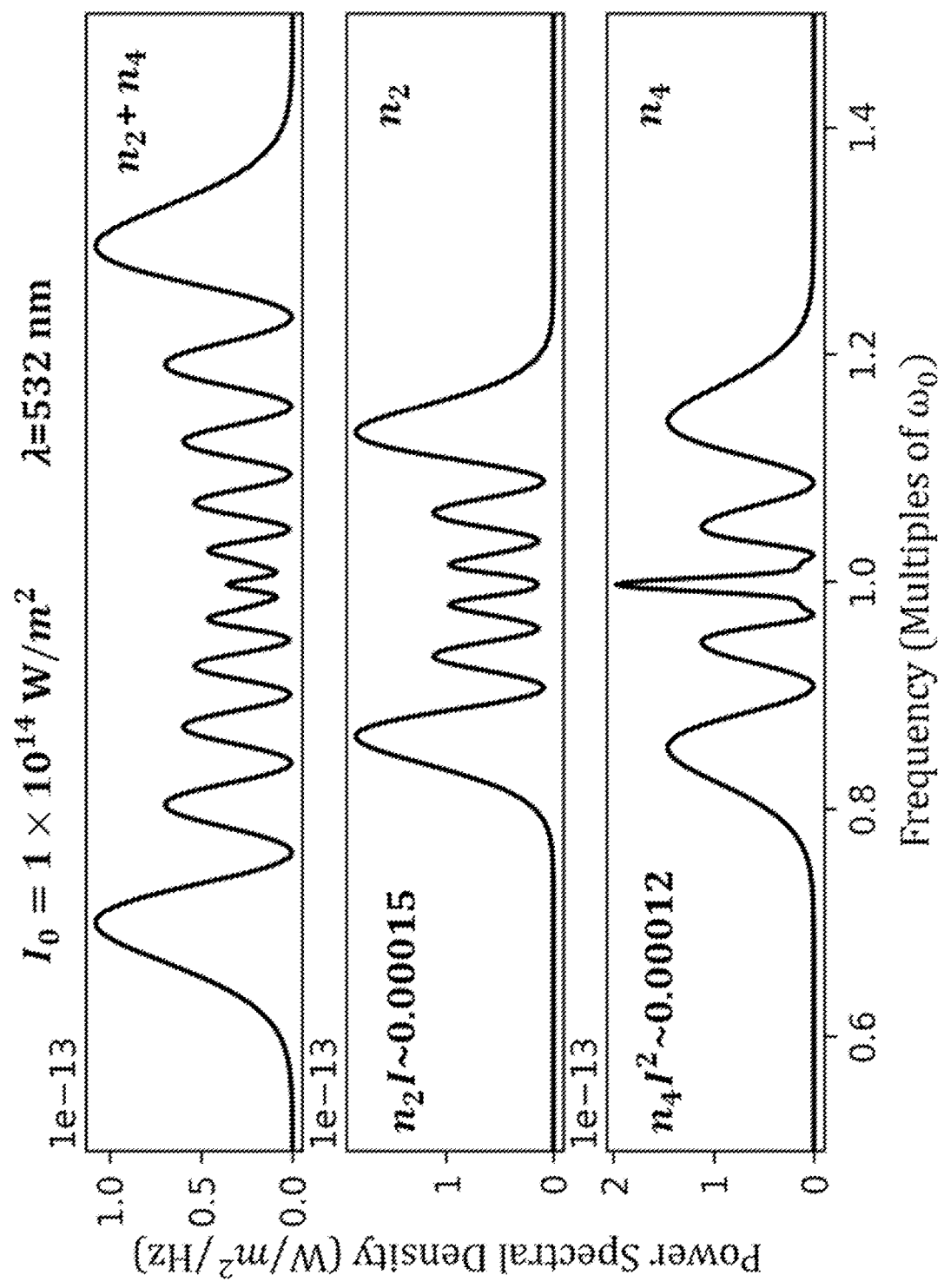
FIG. 1(c) illustrates $CS_2$ spectrum of SPM at $I_0=1\times10^{14}$ W/m$^2$ with central wavelength at 532 nm.
Figure 2:
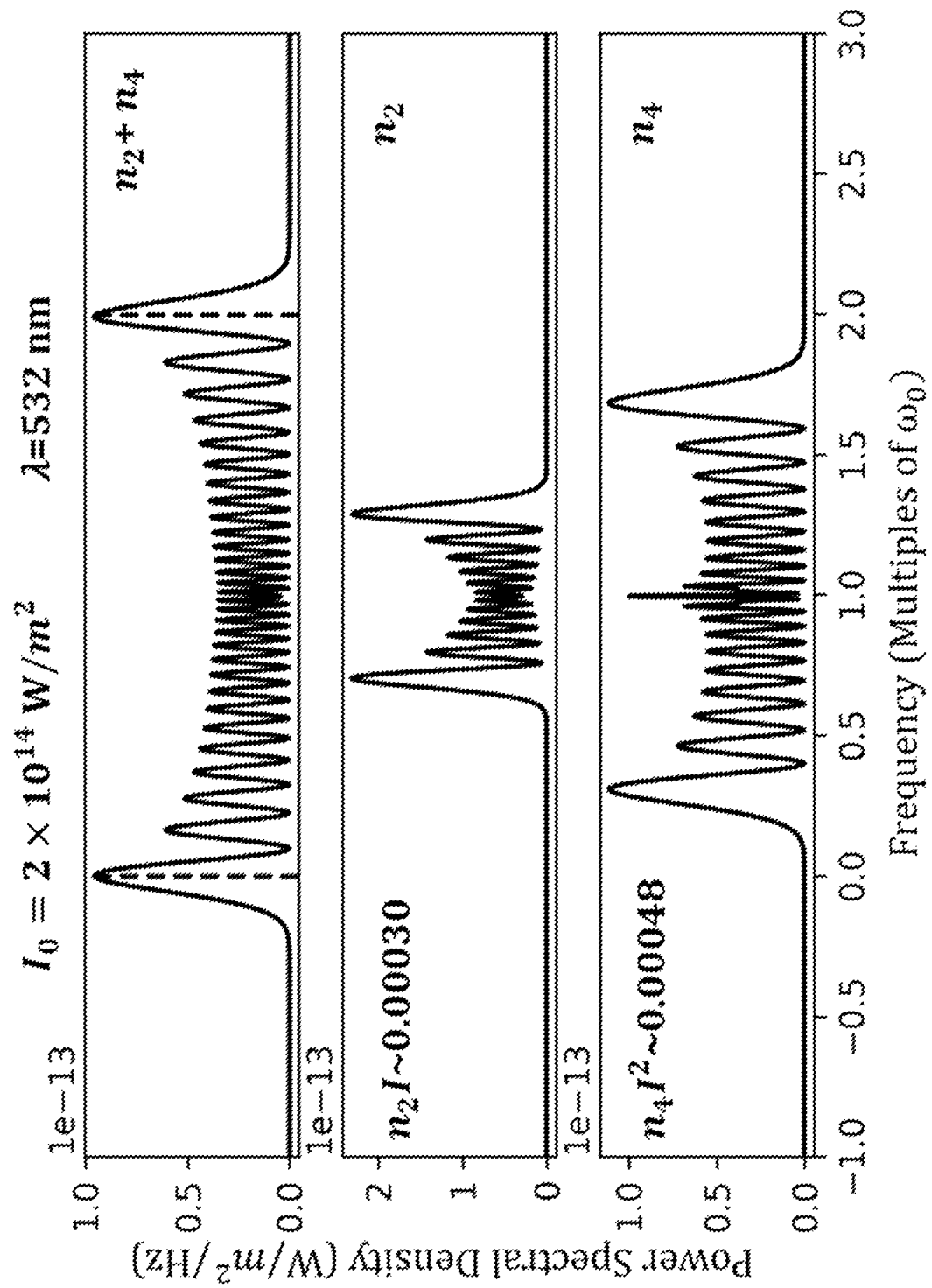
FIG. 2 illustrates $CS_2$ spectrum of SPM at $I_0=2\times10^{14}$ W/m$^2$ with central wavelength at 532 nm.
Figure 3:
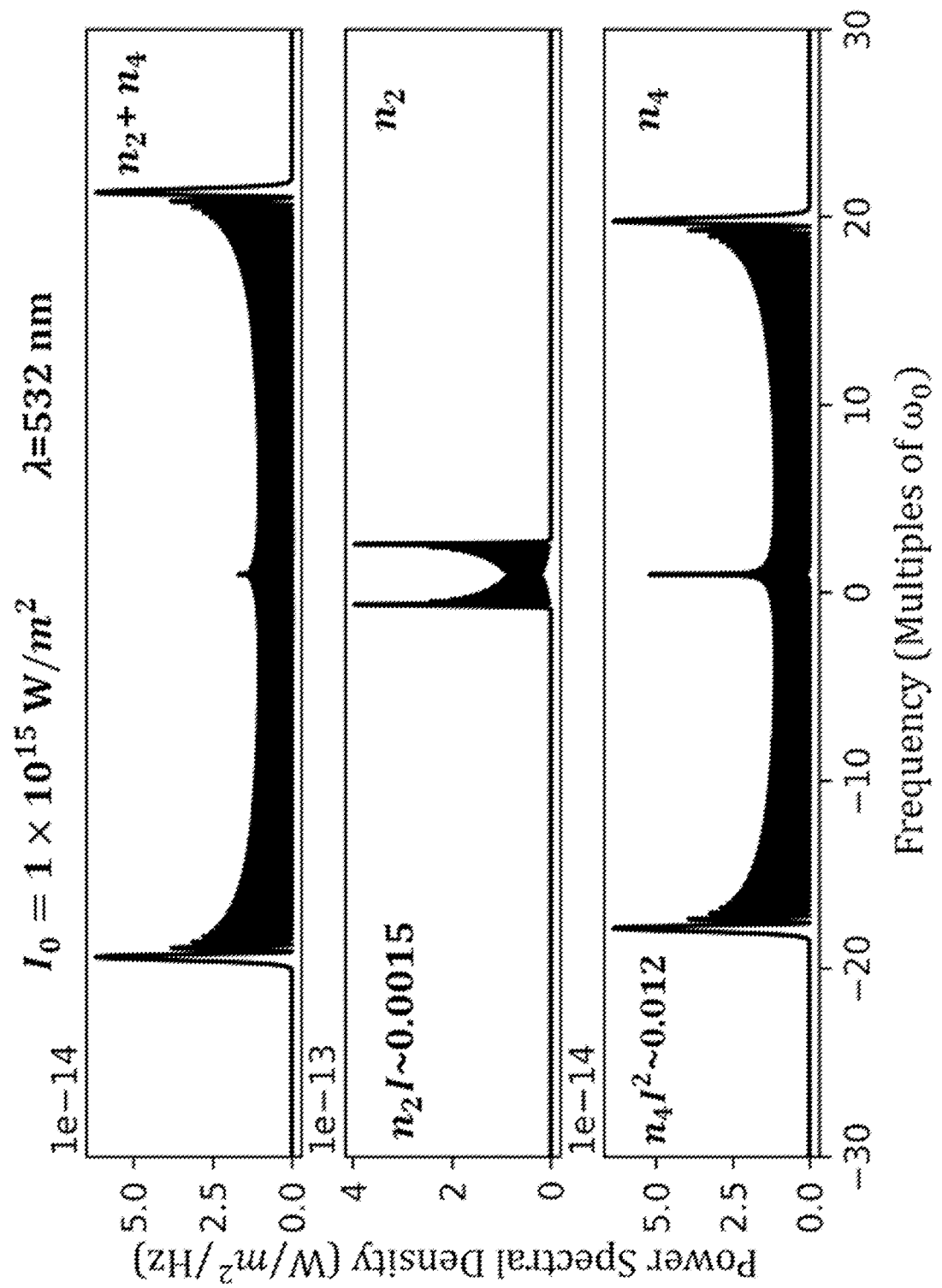
FIG. 3 illustrates $CS_2$ spectrum of SPM at $I_0=1\times10^{15}$ W/m$^2$ with central wavelength at 532 nm.
Figure 4:
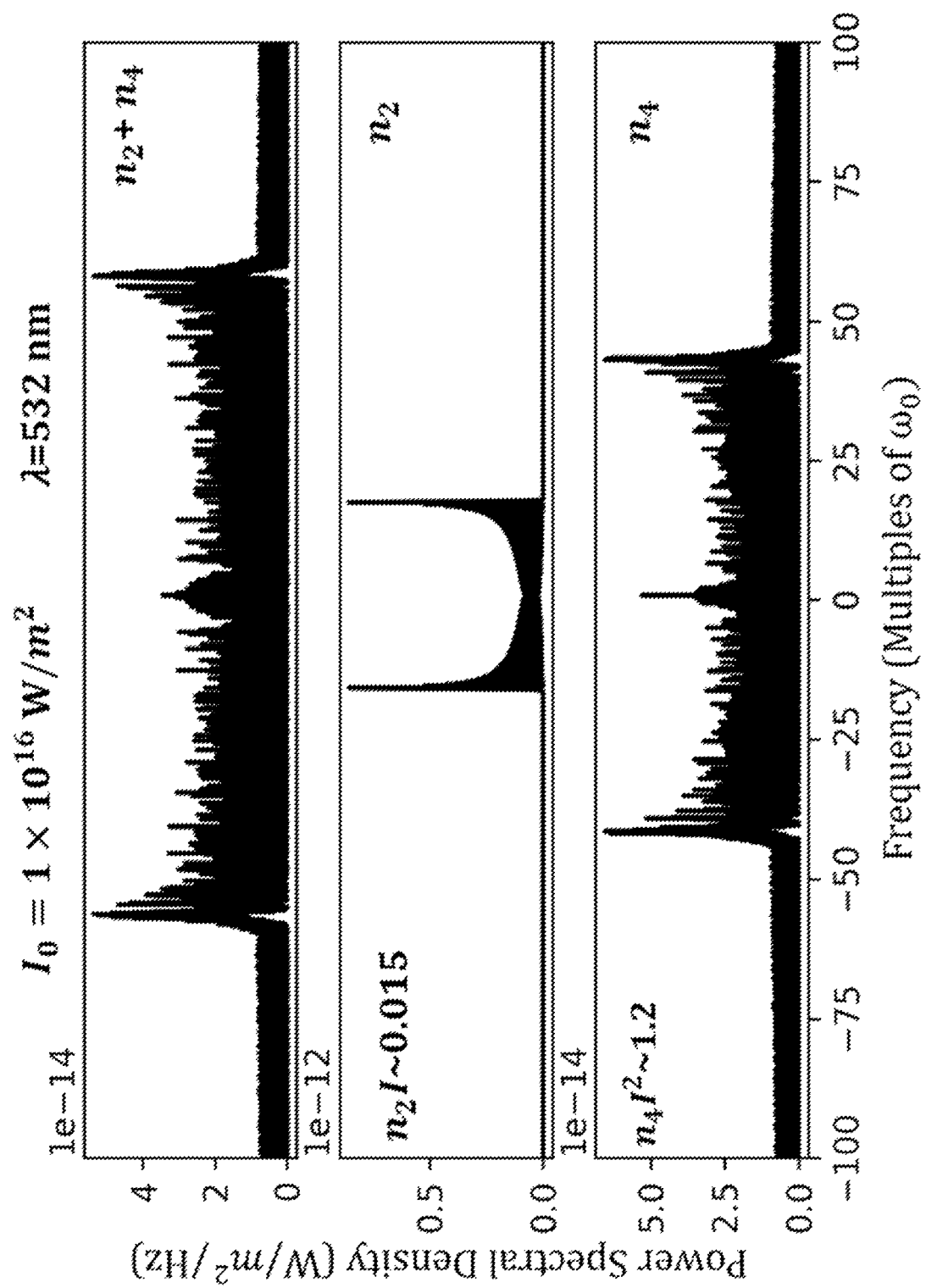
FIG. 4 illustrates $CS_2$ spectrum of SPM at $I_0=1\times10^{16}$ W/m$^2$ with central wavelength at 532 nm.
Figure 5:
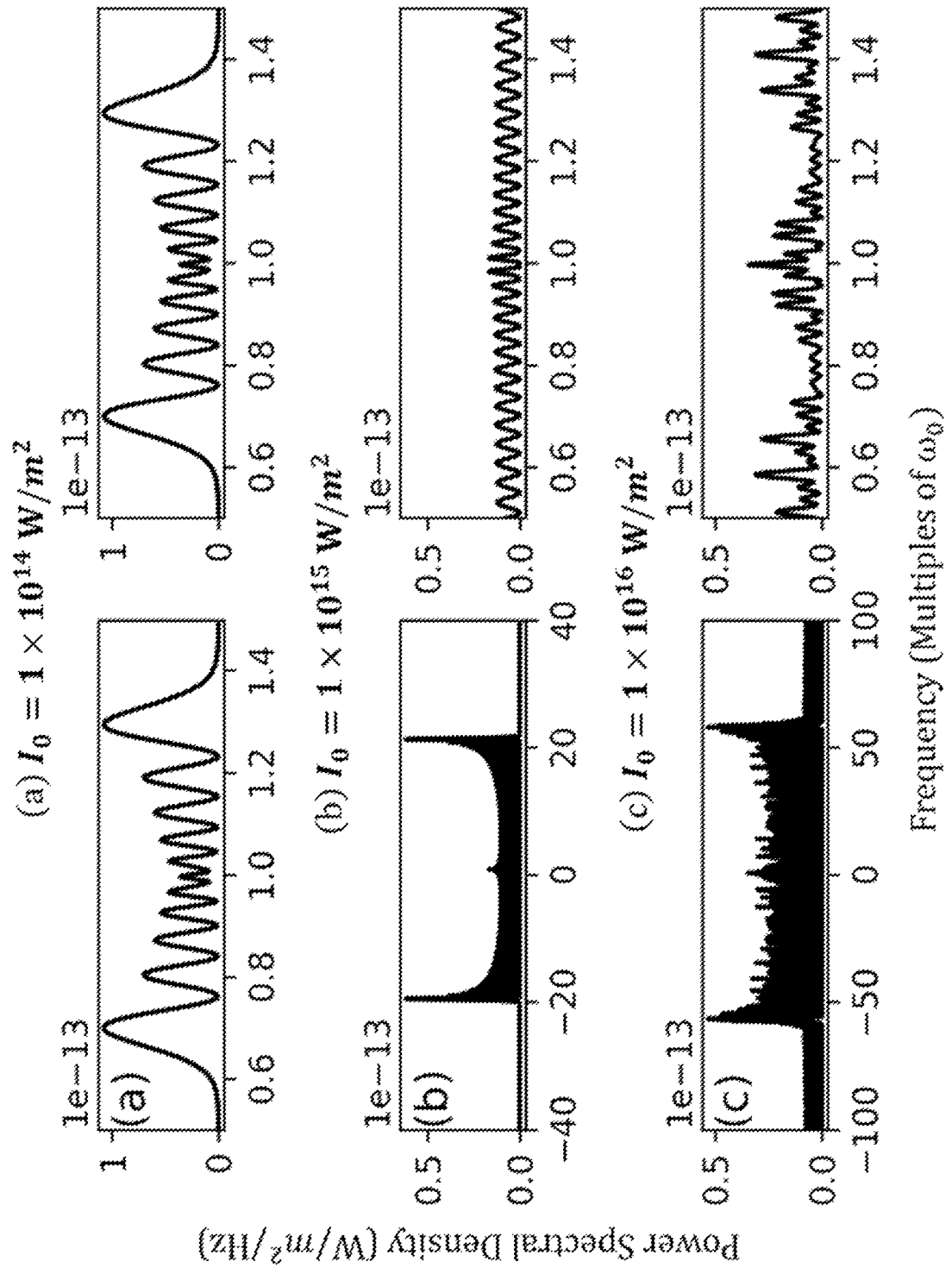
FIG. 5 illustrates $CS_2$ spectra of SPM at (a) $I_0=1\times10^{14}$ W/m$^2$, (b) $I_0=1\times10^{15}$ W/m$^2$, and (c) $I_0=1\times10^{16}$ W/m$^2$ with central wavelength at 532 nm comparing the SPM structure as a whole on the left and within a confined region on the right.

$CS_2$ SPM spectra are created using the same initial beam of 532 nm and 50 fs pulse where $n_0=1.64$, $n_2=1.5\times10^{-18}$ m²/W, and $n_4=1.2\times10^{-32}$ m⁴/W² traveling through $z=1$ cm distance of $CS_2$ in FIGS. 1(C)-5 with the different initial intensity of $I_0=1\times10^{14}$ W/m² [see FIG. 1(c)], $I_0=2\times10^{15}$ W/m² [see FIG. 2], $I_0=1\times10^{15}$ W/m² [see FIG. 3], and $I_0=1\times10^{16}$ W/m² [see FIG. 4]. Each graph of FIGS. 1-4 shows the SPM spectrum with the combined combination of $n_2$ and $n_4$ at the top, contribution of the only $n_2$ at the middle, and contribution of the only $n_4$ at the bottom. FIG. 5 shows the comparison among the SPM spectra presented in FIGS. 1, 3, and 4 within a confined frequency region to show the frequency distribution for the different $I_0$. The frequencies in FIGS. 1(c)-5 are presented as the multiples of the initial frequency ($\omega_0$) in the free space.

FIG. 1(c) shows typical spectral broadening around wo for the Stokes and Anti-Stokes frequencies for the intensity of $10^{14}$ W/m². The salient spectral feature displayed in FIG. 2 shows the frequency extends from $2\omega_0$ to 0 for $2\times10^{14}$ W/m² from Dc to $2\omega_L$. For the higher powers, the SPM spectra go to the negative frequency region in FIGS. 3 and 4. Such negative frequencies might suggest the creation of anti-photon (negative energy) for a higher $I_0$ in SC which can be a matter of interest for future research.

The negative nonlinear refractive index $n_4$ was found at 800 nm due to the $\chi^3$ resonance. Kong [6] experimentally measured $n_2=2.1\times10^{-19}$ m²/W and $n_4=-2\times10^{-35}$ m⁴/W² for 800 nm at the intensity $I_0=1.36\times10^{15}$ W/m² (or 1.36 GW/cm⁻²). To demonstrate the effect of the negative refractive index of SC, a spectrum is produced using Kong's measurements [see FIG. 6] and another spectrum is produced for 532 nm at $I_0=2\times10^{14}$ W/m² with the negative $n_4$ [see FIG. 7] to compare with the effect of positive $n_4$ in FIG. 2.

Figure 6:
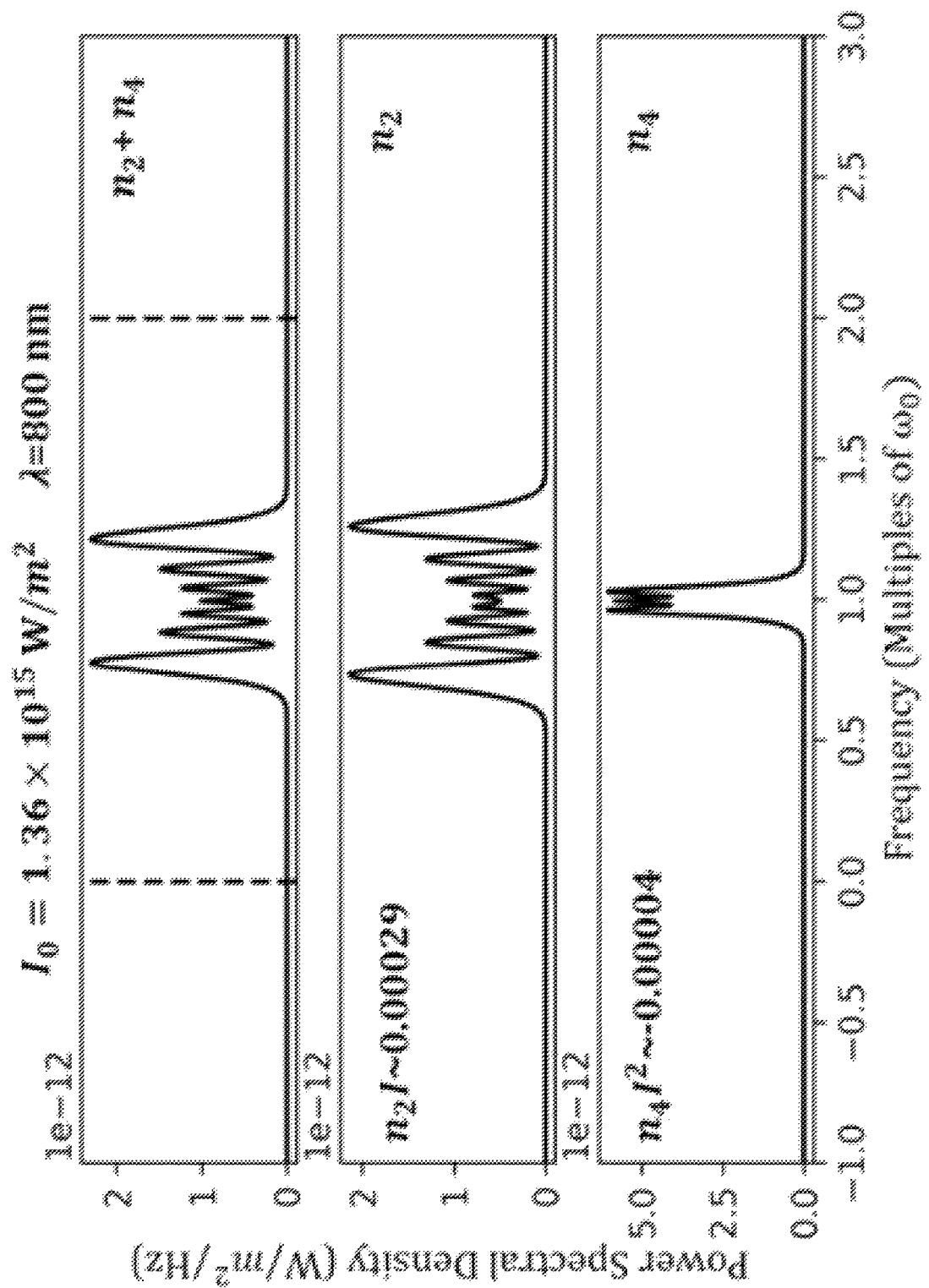
FIG. 6 illustrates $CS_2$ spectrum of SPM at $I_0=1.36\times10^{15}$ W/m$^2$ with central wavelength at 800 nm (with negative $n_4$).
Figure 7:
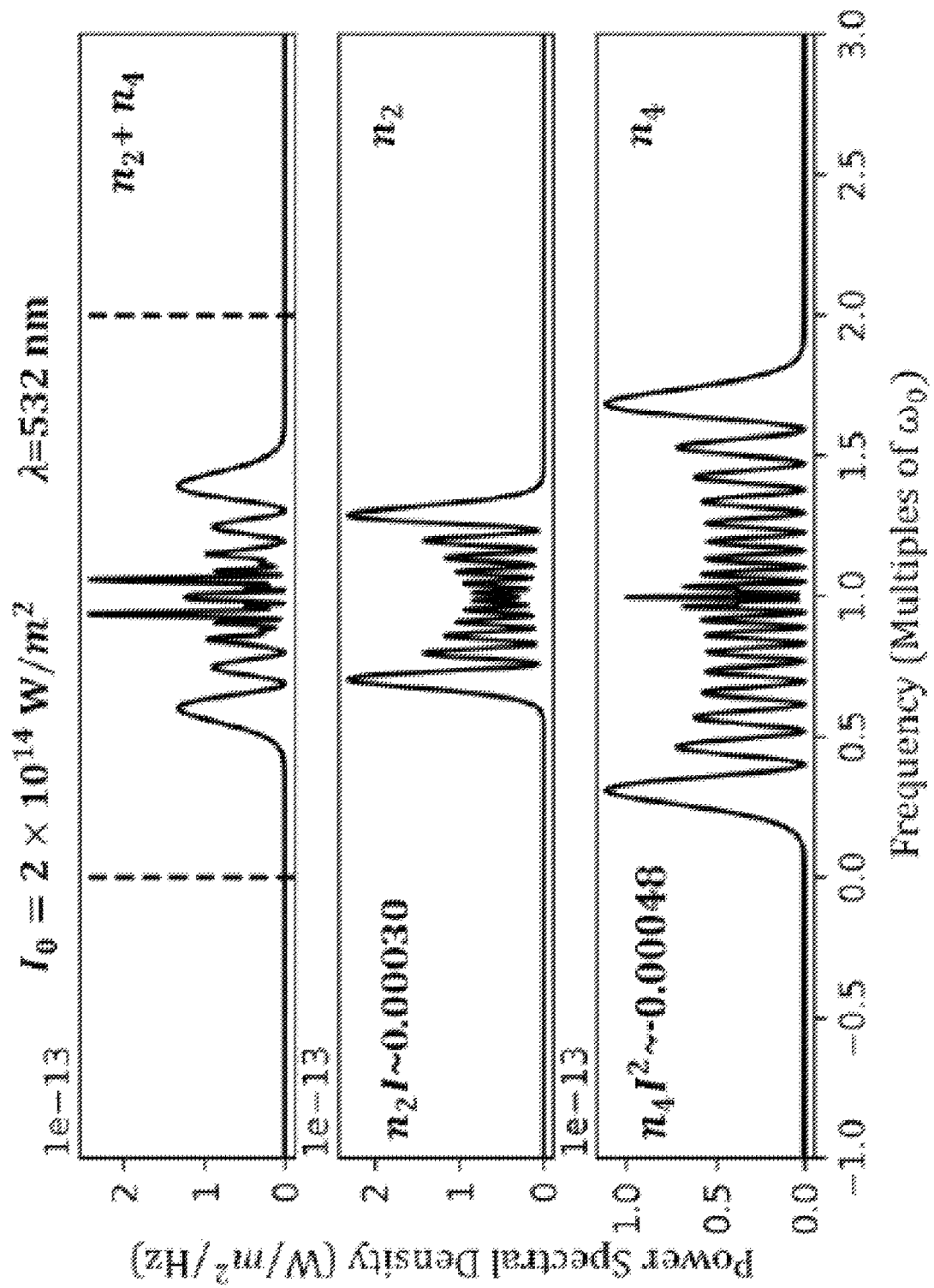
FIG. 7 illustrates $CS_2$ spectrum of SPM at $I_0=2\times10^{1\prime}$ W/m$^2$ with central wavelength at 532 nm (with negative $n_4$).

From Besse [7], $n_4$ is positive at 532 nm and 1064 nm and negative at 800 nm due to the $\chi^3$ resonance. The negative $n_4$ refractive index in both FIGS. 6 and 7 show the interference between the positive $n_2$ and the negative $n_4$. Because of the interference, the combined SPM spectrum span becomes much smaller than the other spectra. At 800 nm, the contribution of the negative $n_4$ is much smaller and effect much less on the contribution of $n_2$ to produce the whole SPM spectrum [see FIG. 6]. To see the side-by-side comparison, an imaginary spectrum is produced assuming the $n_4$ is negative at 532 nm while keeping all values the same [see FIG. 7]. The negative $n_4$ produces the interference with the positive $n_2$ and produces a much smaller SPM spectrum compared to the counterpart [see FIG. 2].

Figure 8:
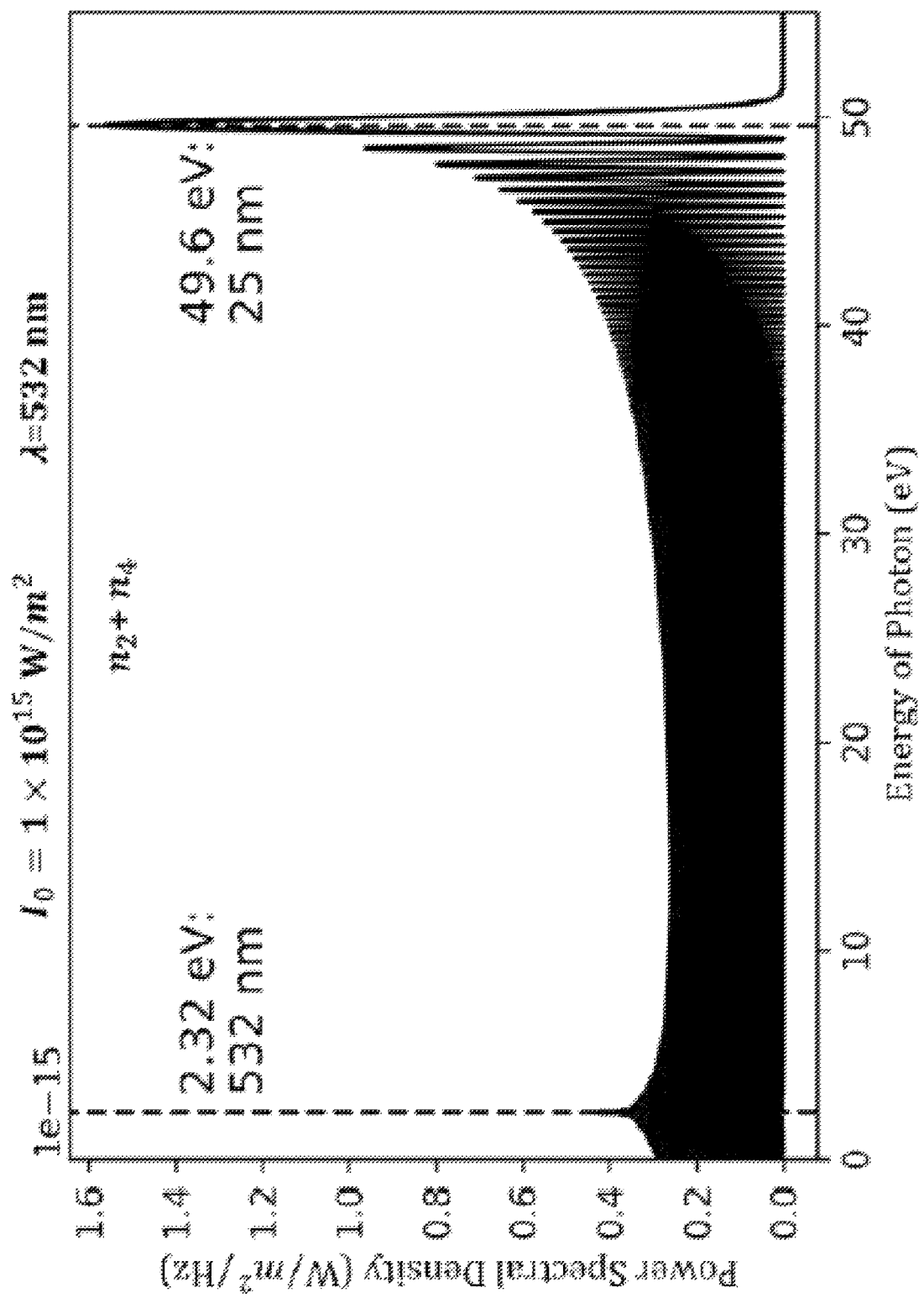
FIG. 8 illustrates $CS_2$ spectrum of SPM in terms of photon energy in eV from D.C. frequency to EUV at $I_0=1\times10^{15}$ W/m$^2$ with central wavelength at 532 nm.

As the pump intensity $I_0$ becomes larger, the contribution of the nonlinear index from $n_4$ ($n_4|I_0|^2\sim0.012$ for $I_0=1\times10^{15}$ W/m² and $n_4|I_0|^2\sim1.2$ for $I_0=1\times10^{16}$ W/m²) becomes larger than $n_2I_0$ term and $n_4$ term dominates on the production of the SPM [see FIGS. 1-4 top and bottom]. For higher intensities such as in FIGS. 3 and 4, the SPM structure goes beyond $2\omega_0$ resulting in an enhanced broadening that can be described as the "Enhanced Ultra-Supercontinuum" (EUSC). FIG. 8 stimulated SC extends from zero Direct Current (D.C.) region near zero to 50 eV into Extreme Ultraviolet (EUV). It is possible to enter the X ray and Gama regions with higher intensities on order $10^{21}$ W/m² (with a Laser beam of 5 mJ with 50 fs at 1 KHz rep rate to spot size of 10 μm to about $10^{17}$ W/cm²). The electronic resonances do not affect the frequency broadening [8].

Figure 9:
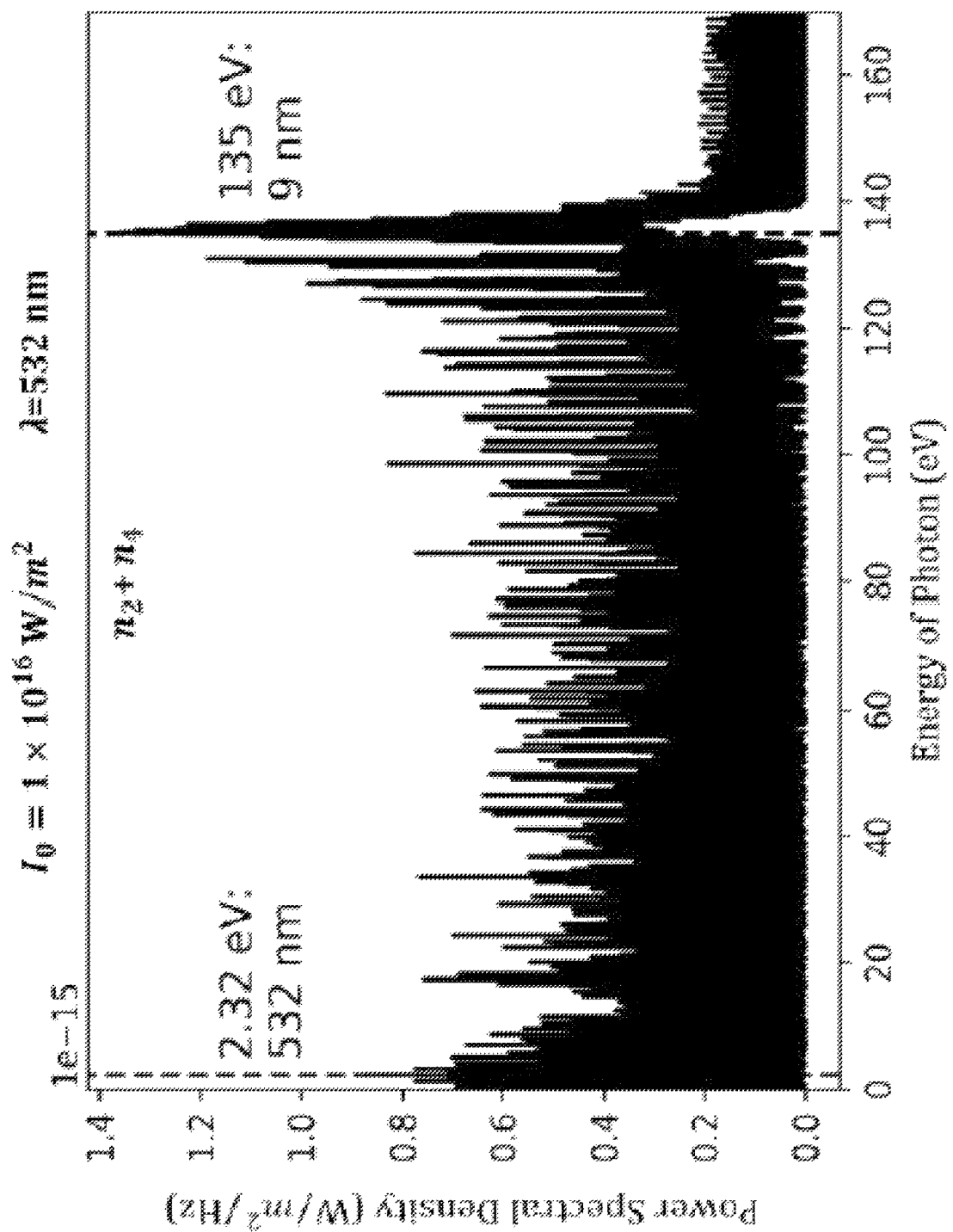
FIG. 9 illustrates $CS_2$ spectrum of SPM in terms of photon energy in eV from D.C. frequency to EUV at $I_0=1\times10^{16}$ W/m$^2$ with central wavelength at 532 nm.

FIGS. 8 and 9 are the modified version of FIGS. 3 and 4 respectively show the energy of the photons showing the positive frequency portion of SC frequency extending from the D.C. region at $\omega_0=0$ to Extreme Ultraviolet (EUV) region (1-100 nm) covering most of EM spectrum. For $I_0=1\times10^{15}$ W/m² [see FIG. 8], the USC extends up to 25 nm/49.6 eV (~20 $\omega_0$). A very interesting USC spectrum can be observed when the effect of $n_4$ comes close to no (1.2~1.4) for higher intensity, $I_0=1\times10^{16}$ W/m² [see FIG. 9]. For such spectrum, the EUSC extends up to 9 nm/135 eV (~60 $\omega_0$) and after 9 nm peak, a trail of low-intensity peaks continues beyond 2000 eV into the soft X-ray region. These low-intensity peaks might be hard to detect by the detector while detecting EUSC peaks. Such EUSC generation up to the EUV is both predicted in Helium atoms and observed in Argon atoms.

Part 2

In the second part, we teach the index of refraction n(t) follows the instantaneous temporal response of the nonlinear index following the optical cycle which causes HHG and spectral broadening.

Over the past twenty years, there have been extensive experimental observation, from pioneers like Corkum [9], on generating the odd harmonics and the production of attosecond pulse from rare gases using extreme ultrafast lasers beams and theoretical models based on semi-classical and quantum theory but without giving the shape of higher harmonic generation (HHG) [9,10]. The HHG produced attosecond pulse has been used for the applications like probing the and the notion of generating attosecond pulses using Fourier synthesis has been speculated by implementing high harmonic generation to mimic the mode-locked laser mechanism.

We introduce an Ansatz that the index n follows the optical cycle of the phase not envelope. This electronic self-phase modulation (ESPM) model is more fundamental than the slow varying envelope approximation (SVEA) of nonlinear approximation and nonlinear Schrödinger equation (NLSE) from Maxwell Equation where the envelope is followed. These approximations break down for electron clouds response of $n_2$ where the response time is to the carrier envelope phase (CEP) on the optical cycle response. We have extended the pioneering research of John Kerr and Buckingham [4] on the traditional DC and AC electronic voltage switching device to modulate and alter the polarization of a light based on the rapid response of organic liquids to the applied electric field E to pair of electrodes. The original Kerr gates are based on the index of refraction becomes electric field E dependent:

$$n(t)=n_0+n_2\{E(t)\}^2, \quad (11)$$

where $n_0$ is the index of refraction, $n_2$ is the nonlinear index and E is the electric field (can be DC or AC). In 1956, Buckingham proposed a higher frequency optical Kerr effect when an intense linearly polarized light beam traveling through an optical isotropic medium in the material becomes temporal anisotropic. He extended Kerr's idea by assuming instantaneous response of the molecules to the applied electric field in terms of the modulating refractive index over time. A major advance occurred when Duguay in 1969 realized this experimentally by extending the traditional DC/AC Kerr and theoretical proposed optical Kerr effect processes into the optical regime where E is the optical field from a 10 ps laser pulse; and it now is called the Optical Kerr Gate. In fact, the index of refraction n arises from the underlying electronic states transition from among all states available from virtual and real as per quantum processes. So, the Ansatz assumption given for n and nonlinear counterpart is more fundamental than that derived from a wave equation approximation.

In the Kerr effect, the material behaves optically as though it were a uniaxial crystal in which the electric field of the laser acts as an optic axis. The major mechanisms responsible for inducing birefringence can arise from distortion of electron clouds, rotations of molecules, and disturbance of the molecular motion. The Optical Kerr gate has been used extensively as an ultrafast optical gate. While propagating, an intense optical pulse changes the index of refraction by causing the direct distortion of the electronic cloud and the molecular motion. The change in index leads to spectral broadening from self-phase modulation (SPM).

Alfano and Shapiro, using 532 nm picosecond pulses made a startling observation and discovery of supercontinuum and attributed it to SPM and self-focusing on various crystals, liquids, and glasses, including liquefied and solidified rare gases. They showed that the electronic mechanism for SPM is important in all materials and dominates all other processes in some materials, e.g., even in rare noble liquid Argon, and Krypton.

The electronic distortion mechanism from quantum transitions is present in all condensed and gases material, a fact consistent with the experimental observation of SPM spectra in all samples studied under intense ultrafast laser excitation.

Two main theories were expounded to explain HHG process: a complex phenomenological nonmathematical explanation for high ultrafast pulse interaction proposed by Corkum [9] first followed by many other for semi-classically by a three-step model, and a quantum-mechanically Schrodinger dipole E·r approximation approach by Lewenstein [10]. The cutoff energy of HHG was related to $I_P+3U_P$, the ionization ($I_P$) and potential ($U_P$) energy to remove electrons for a single electron model. This model has been explained as follows: Ionization of electron, the high-intensity laser field ($10^{14}$ to $10^{16}$ Wcm$^{-2}$); the electron tunnels through the electric potential barrier; acceleration of the free electron, the free electron generated by tunneling with a zero initial velocity is accelerated away from the parent ion by the driven field; then finally, the electron is driven back to the parent ion. These explain the 3 regions of odd high harmonics (HH). However, this process lacks basic physical insight for new materials and a better mathematical and theoretical explanation is needed. So, the Ansatz based on ESPM model was developed from nonlinear index arising from intense ultrafast E-field and this index responses to the optical cycles of the carrier envelope phase (CEP). Such instantaneous response is quantum mechanical because $n_2$ for noble gases respond from the electron cloud, which is faster than 150 attoseconds, the Bohr orbital time to about 30 attoseconds.

An alternative Ansatz theoretical model to Lewenstein's is presented in support of the ESPM direct-electron cloud distortion model of SPM for $n_2$ from $\chi^3$ to give rise to odd HH. The HHG modes generation leads to locking in-phase of these N modes to generate attosecond pulses by Kerr mode-locking in rare noble gas atoms, like Argon (Ar), Krypton (Kr), Nitrogen ($N_2$), Oxygen ($O_2$) in gaseous, liquid, and condensed states of matter. These materials can be placed in a hollow microfiber to enhance the interaction length.

After an intense light beam propagates a distance z into the material, the electric field is distorted in the CEP and has the form:

$$E(t) = E_0 e^{-\frac{t^2}{T^2}} \cos[\phi(t)], \quad (12)$$

where, $$T = \frac{\tau_p}{\sqrt{2\ln 2}},$$

$\tau_p$ is the full width half maximum (FWHM) of the pulse, and the modulated instantaneous phase of CEP under the envelope is given by, $$\phi(t) = \omega_0\left\{t - \frac{n(t)z}{c}\right\} + \varphi, \quad (13)$$

where $\omega_0$ is the central angular frequency of the laser, n(t) is the refractive index, z is the propagating distance, and $\varphi$ is the offset phase. The offset CEP phase is set to be zero for the cosine-like pulse which drives HHG modes. Following Alfano et al. [3,11] and Buckingham [2] without averaging over cycles, the general form for the Kerr Equation (12) is given by the nonlinear refractive index with quadratic field dependence and the response time $\tau$ which is, $$n(t) = n_0 + \int_{-\infty}^{t}\int_{-\infty}^{t} f(t',t'') E(t-t') E(t-t'') dt' dt'', \quad (14)$$

where, $n_0$ is the ordinary index, E the electric field and, $$f(t', t'') = \left(\frac{n_2}{\tau}\right) e^{-\frac{t'}{\tau}} \delta(t - t''), \quad (15)$$

where, $n_2$ is the nonlinear index. Equation (14) may be simplified to $$n(t) = n_0 + \left(\frac{n_2}{\tau}\right) \int_{-\infty}^{t} e^{-\frac{(t-t')}{\tau}} E^2(t') dt'. \quad (16)$$

The pure electronic mechanism of $n_2$ for rare noble gases like Ar, Kr, and Ne involves no translation of nuclei or rotation of atomic cluster and is expected to have relaxation response time much less than the optical period $$\left(\ll \frac{1}{\omega_0}\right),$$

faster than 150 attosecond on the order of zeptoseconds scale. For this case, the index n(t) responses to E(t) at optical frequencies. Hence the weighting function $$\left(\frac{1}{\tau}\right) e^{-\frac{(t-t')}{\tau}}$$

may be replaced by $\delta(t-t')$. Following Eq. (11) for the Kerr effect, the electronic response of the nonlinear index becomes:

$$n(t) = n_0 + n_2 \left[E_0 e^{-\frac{t^2}{T^2}} \cos\phi(t)\right]^2, \quad (17)$$

which represents the instantaneous response of the index of refraction. Equation (17) is the ansatz that has been used before in the form of n by luminaries like Kerr and Buckingham. The ansatz n(t) follows the modulation optical cycles of the phase of E. The instantaneous response is used to follow the optical cycle rather than the envelope of the CEP without time averaging.

This ansatz is a good assumption since the outcome as shown in the electronic SPM leads to experimentally observed three regimes of HHG and cutoff frequency can be calculated based on this ansatz using the method of stationary phase for noble rare molecules like Argon and Krypton. The fact that n follows the optical cycle of the phase, not the envelope is more fundamental than slow varying envelope approximation (SVEA) of nonlinear approximation and nonlinear Schrödinger equation NLSE from Maxwell Equation where the envelope is followed. These approximations break down for electronic response of $n_2$ where the response to optical cycle modulation.

Substituting Eq. (17) into Eq. (12) and Eq. (13), the electric field E(t) becomes electronic self-phase modulated at z and is given by:

$$E(t) = E_0 e^{-\frac{t^2}{T^2}} \cos\left[\omega_0\left(t - \frac{n_0 z}{c}\right) - \beta e^{-\frac{2t^2}{T^2}} \cos^2\left(\omega_0\left(t - \frac{n_0 z}{c}\right)\right)\right], \quad (18)$$

where $$\beta = n_2 E_0^2 \left(\frac{\omega_0 z}{c}\right).$$

Figure 11:
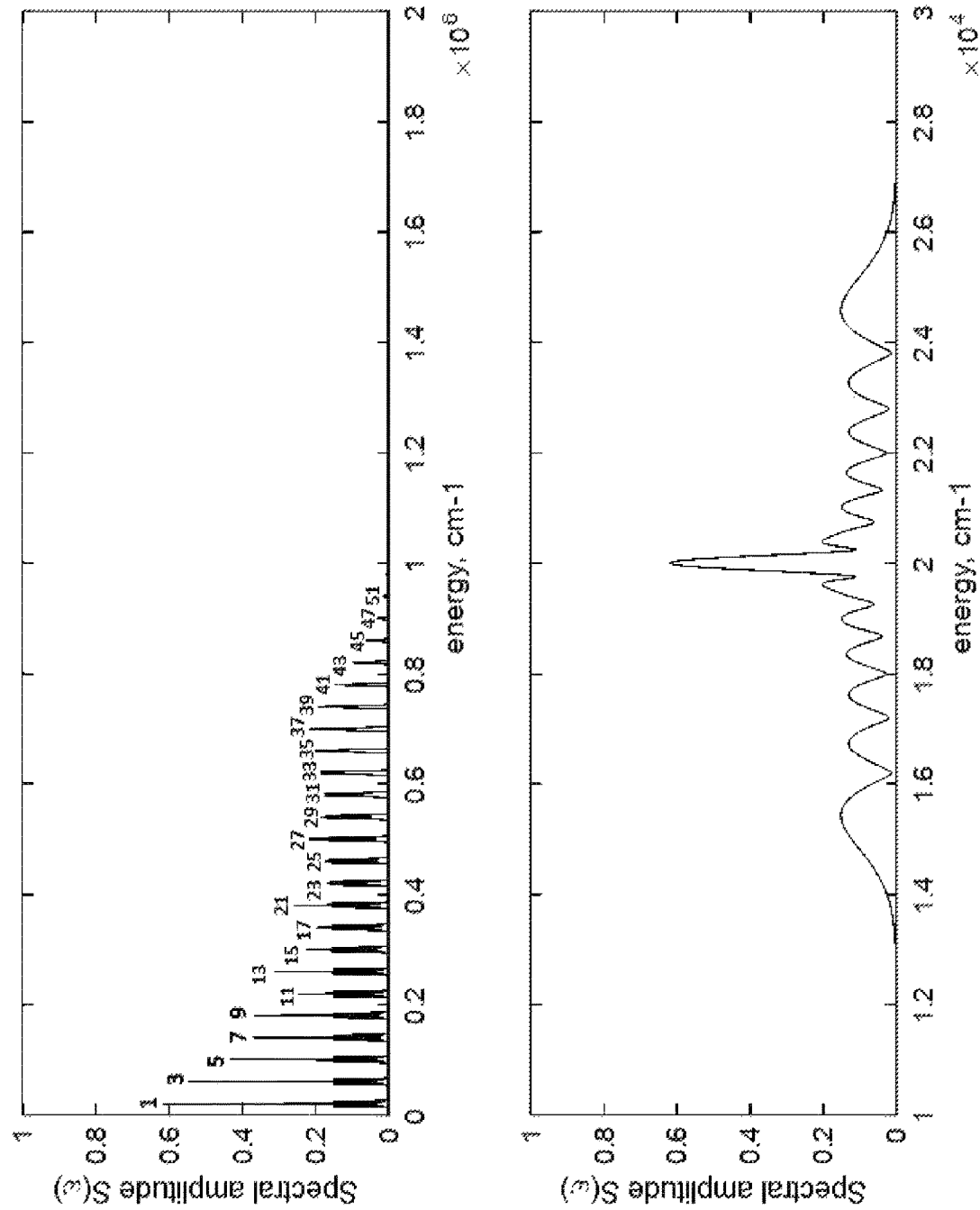
FIG. 11 illustrates spectral amplitudes of electric field after propagation of 6.5 mJ pulse through 0.5 mm thickness of Ar gas. The bottom plot shows the spectral amplitude of the first harmonics (zoomed area of the upper plot).
Figure 12:
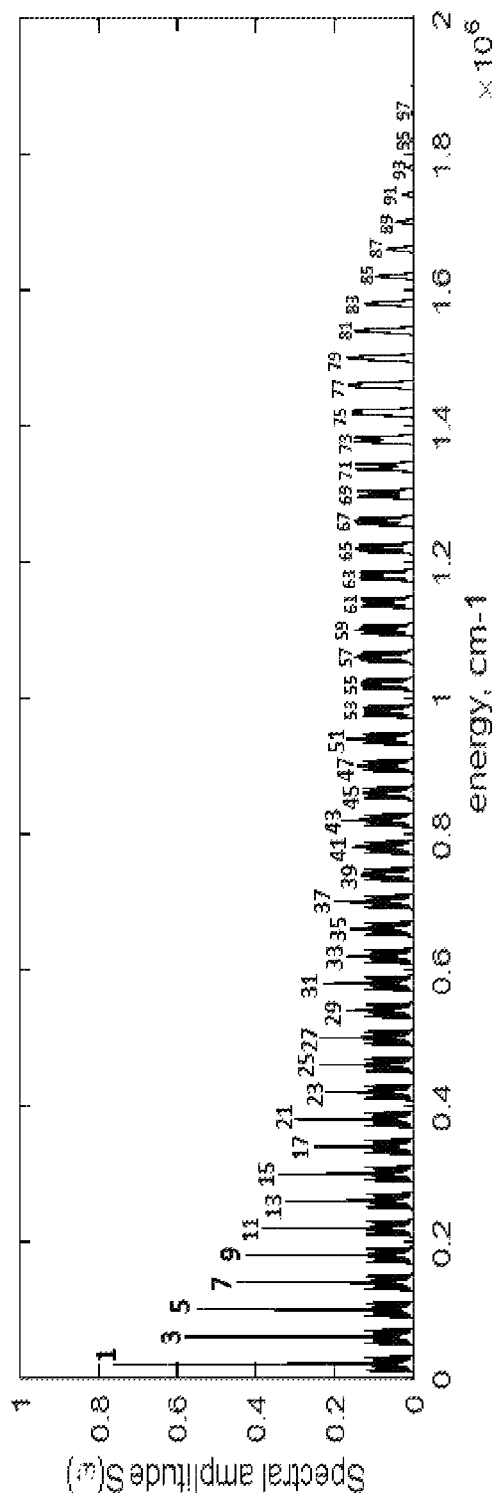
FIG. 12 illustrates spectral amplitudes of electric field after propagation of 13 mJ pulse through 0.5 mm thickness of Ar gas. The bottom plot shows the spectral amplitude of the first harmonics (zoomed area of the upper plot). The same plot can be obtained with a pulse energy of 6.5 mJ and double propagation distance (1 mm).
Figure 12:
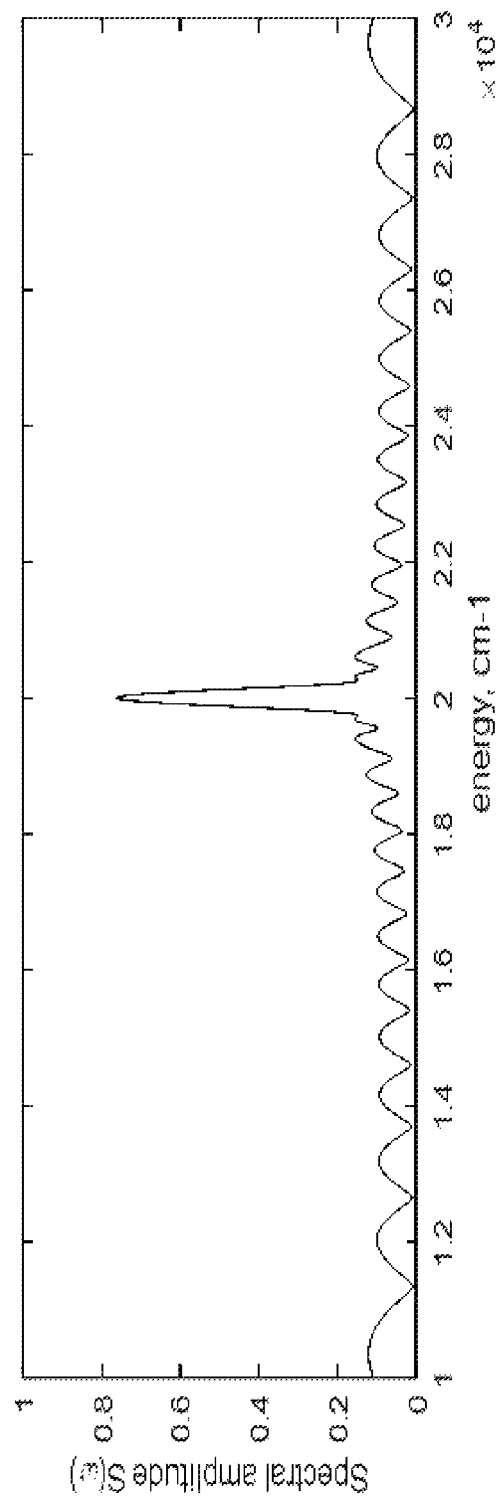

From Eq. (18), E(t) results in Bessel function expansion resulting in odd harmonics and spectral broadening. In addition, from Eq. (18), the electronic self-phase modulated spectral $E(\omega)$ is obtained by the Fast Fourier Transform (FFT) technique resulting in odd harmonics from the cosine of a cosine squared function. The spectral density of the phase-modulated light is:

$$S(\omega) = \frac{c}{4\pi} |E(\omega)|^2, \quad (19)$$

where $E(\omega)$ is the Fourier transform of E(t) which is shown in FIGS. 11 and 12 showing the three characteristic features of the odd HHG with the cutoff frequency.

In the case of the rare gas molecule that possesses spherical symmetry, a pure electronic mechanism for the nonlinear index $n_2$ involves no translation of nuclei, libration, or rotation of atomic clusters and is expected to have a relaxation time much less than the optical period. Buckingham and coworkers elaborate on induced dipole moment from nonlinear hyperpolarization arising from electronic distortion of the inert atom which occurs from intense electric fields.

Figure 10:
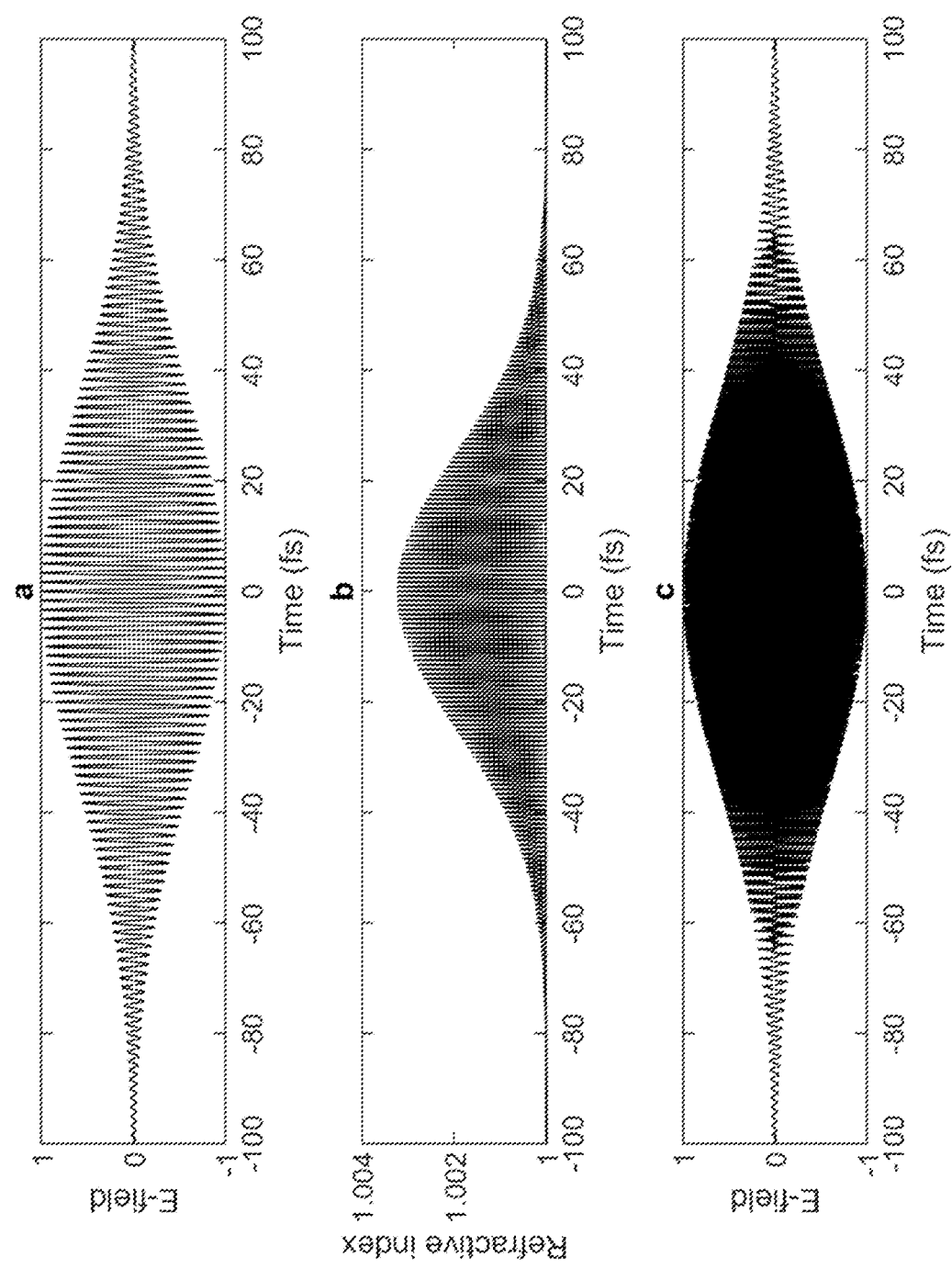
FIG. 10 illustrates from top to bottom: Electrical field of the incident pulse; modulation of refraction index; electrical field after propagation of 6.5 mJ pulse through Ar gas of 0.5 mm thickness.

A self-phase modulation about wo is shown in FIG. 10 for a 500 nm, 80 fs input beam with the pulse energy of 6.5 mJ and 13 mJ with a beam radius of 20 μm. The spectra calculated for Ar ($n_0$=1 and $n_2$=2.5×10$^{-19}$ cm$^2$/W) from Eq. (18) and (19) shows odd harmonic peaks up to N [see FIGS. 11 and 12] arising from electronic self-phase $n_2$. The N harmonic peaks are separated by $2\omega_0$. Several odd N for the Fourier transform bandwidth pulse $\tau_p$ from a 500 nm and 50 fs beam gives more than 31 HH peaks [see FIGS. 11 and 12]. These odd HHG looks like a mode-locked laser train except the modes are not separated by $$\frac{c}{2L},$$

but by $2\omega_0$ and using the relation:

$$E(\omega) = \sum_{n=0}^{N} \delta(\omega - \omega_{2n+1}) e^{-i(\omega_{2n+1} t + \phi)}; \quad (20)$$

summing over odd n from 1 to N, where φ is an arbitrary number. The Kerr mode locking occurs from these deltas like HHG peak which is driven by intense laser pulse. The phases are locked by the Kerr index n2 with the aperture and/or beam confinement to give attosecond pulse from the transform-limited of Gaussian relation:

$$\tau_p = \frac{0.4}{N(2\omega_0)}, \quad (21)$$

for N=31 coupled modes driven by the intense pump beam, the Kerr mode-locking from $n_2$ gives $\tau_p$ of 20 attoseconds.

FIG. 10 shows the electric field of the incident beam, the refractive index from the Ar gas, and the modulated electric field of the beam after going through the Ar gas. FIG. 11 and FIG. 12 show the spectral amplitude vs. wavenumber with the higher harmonic modes and the first HHG mode for different pulse energies, respectively. The spectra consist of a set of odd higher harmonics, each of them is broadened because of the self-phase modulation of each harmonic. The outcome from ESPM is a supercontinuum background superimposed with the sharp HHG which was experimentally observed.

FIG. 12 shows HHG after doubling the incident beam energy of FIG. 11. The same result can be achieved by doubling the propagation distance as well. The electronic SPM $n_2$ model shows the three regions observed in HHG. Both figures show the same HHG structure of three phases with the plateau and cutoff regions like that has been experimentally observed in solid Argon, Krypton, and others.

Figure 13:
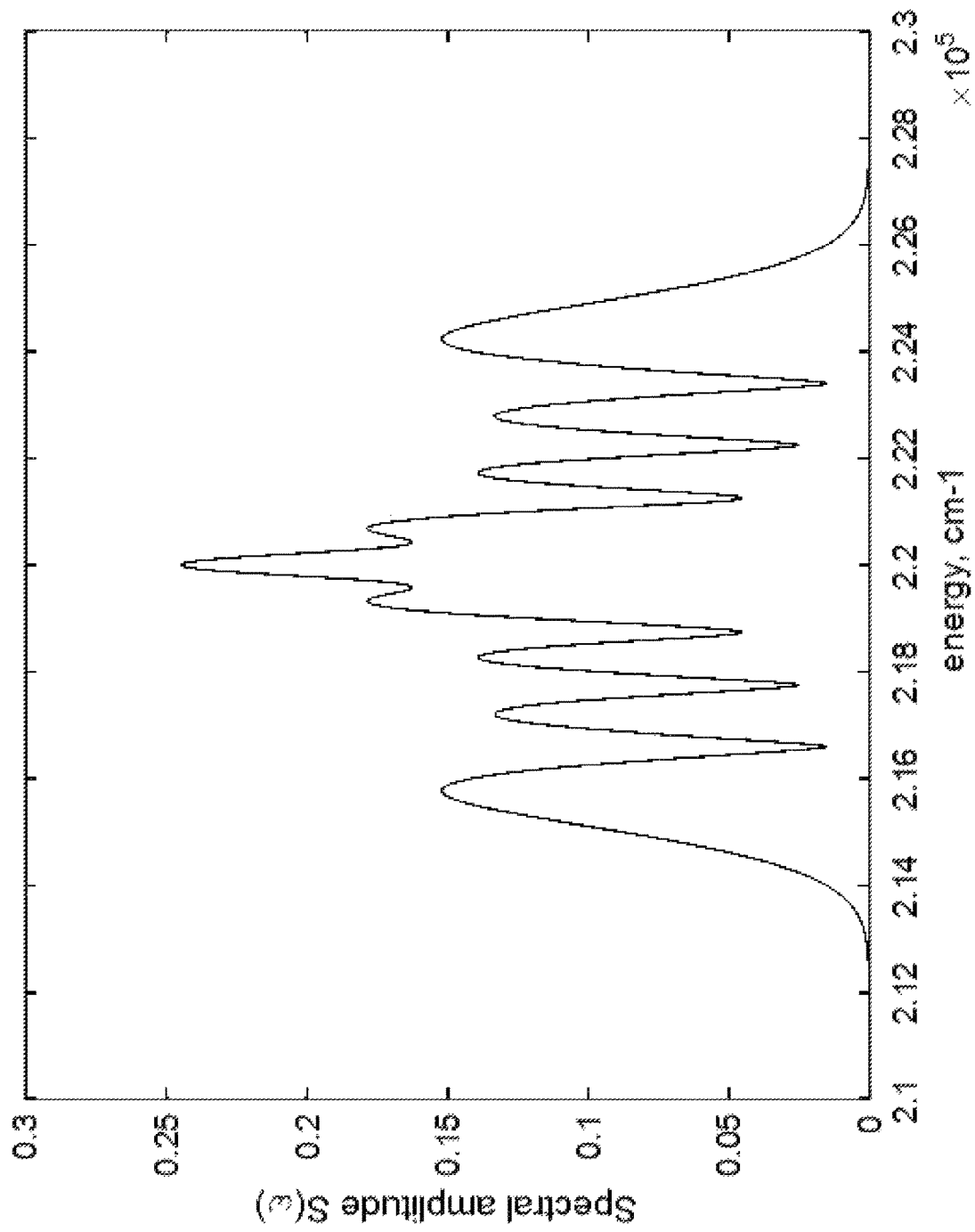
FIG. 13 illustrates spectral amplitude of 5th harmonic ($\omega=11\omega_0$).

FIG. 13 shows the 5th harmonic pattern like FIG. 11 and FIG. 12. Compared to the first harmonic, the central frequency of the 5th harmonic has almost one-fourth of the intensity. Although both have a similar spectral SPM broad sideband structure with spectral oscillations about the 5th harmonic, these spectral patterns about HH should be observed as the fingerprint of electronic $n_2$ SPM.

To find the cutoff frequency $\omega_{max}$ for HHG according to the ESPM theory, we use the method of stationary phase. The frequency spectrum of the beam propagating through a medium with the spherical atoms/molecules like rare gas molecules of Ar and Kr that give the electronic response to the optical cycle the propagating E(t) beam can be described by Fourier transform as, $$E(\omega) = \frac{\text{Re}}{2\pi} e \int_{-\infty}^{+\infty} E_0(t) e^{-i\left(\omega_L t - \frac{\omega_L n z}{c}\right)} e^{i\omega t} dt, \quad (22)$$

where z is the propagating distance into the medium, $\omega_L$ is the laser angular frequency, $E_0(t)$ is the time-dependent envelope of the propagating electronic field of the beam and, the refractive index n can be found from Eq. (17).

Combining Eq. (17) with Eq. (22) will give, $$E(\omega) = \frac{\text{Re}}{2\pi} e^{\frac{in_0\omega_L z}{c}} \int_{-\infty}^{+\infty} E_0(t) e^{i\left((\omega-\omega_L)t + \frac{\omega_L z}{c}\left[n_2\left(E_0 e^{-\frac{t^2}{T^2}} \cos\omega_L t\right)^2\right]\right)} dt. \quad (23)$$

The integral at Eq. (23) is the like integral used by the method of stationary phase [13] as, $$f(x) = \int_\alpha^\beta g(t) e^{ixh(t)} dt, \quad (24)$$

which can be approximately evaluated by the method of stationary phase for h(t). Equation (23) and Equation (24) will give:

$$h(t) = (\omega - \omega_L)t + \frac{\omega_L z}{c}\left[n_2\left(E_0 e^{-\frac{t^2}{T^2}} \cos\omega_L t\right)^2\right]. \quad (25)$$

The first derivation of h(t) is given by, $$h'(t) = (\omega - \omega_L) + \frac{\omega_L z}{c} n_2 I_0 \left[ e^{-\frac{2t^2}{T^2}}\left(-\frac{4t}{T^2}\right)\cos^2\omega_L t + e^{-\frac{2t^2}{T^2}}(2\cos\omega_L t)(-\omega_L \sin\omega_L t)\right]. \quad (26)$$

For method of stationary phase $\dot{h}(t)=0$ will yield the frequency extend in time:

$$(\omega - \omega_L) = \frac{\omega_L z}{c} n_2 I_0 e^{-\frac{2t^2}{T^2}}\left[\left(\frac{4t}{T^2}\right)\cos^2\omega_L t + \omega_L \sin 2\omega_L t\right]. \quad (27)$$

At maximum values, $\cos^2\omega_L t=1$ and $\sin 2\omega_L t=1$, putting such values at maximum in Eq. (27) will give, $$(\omega - \omega_L)_{max} = \frac{\omega_L z}{c} n_2 I_0 e^{-\frac{2t^2}{T^2}}\left[\frac{4t}{T^2} + \omega_L\right]. \quad (28)$$

At the critical point t=0, Eq. (28) for maximum HHG extent becomes, $$(\omega - \omega_L)_{max} = \left[\frac{\omega_L}{c} n_2 I_0 z\right] \omega_L \propto I_0 \omega_L^2. \quad (29)$$

Using $$\frac{\omega_L}{c} = \frac{2\pi}{\lambda},$$

where c=speed of light in vacuum, Eq. (29) can be written as $$(\omega - \omega_L)_{max} = \left[\frac{2\pi}{\lambda} n_2 I_0 z\right] \omega_L. \quad (30)$$

The cutoff frequency of the HHG: $(\omega-\omega_L)_{max}$ depends on $n_2$, the intensity $I_0$, z, and $\omega_L^2$.

For example, when a 500 nm beam with the pulse energy of 6.5 mJ goes through 0.5 mm in Ar ($n_0=1$, $n_2=2.5\times 10^{-19}$ cm$^2$/W, $I_0=2.6\times 10^{16}$ W/cm$^2$) gas, the cutoff frequency of the higher harmonics from Eq. (28) would be, $$(\omega-\omega_L)_{max} \approx 41\, \omega_L. \quad (31)$$

Using the inflection point of the envelope, another cutoff frequency can be calculated which is shown in the supplementary part of the paper.

Thus, a simple equation for the cutoff frequency for HHG generation can be analytically produced from ESPM theory using the method of the stationary phase. It depends on physical $n_2$, $\omega_L$, z, and peak intensity rather than $I_P$ and $U_P$.

Figure 14:
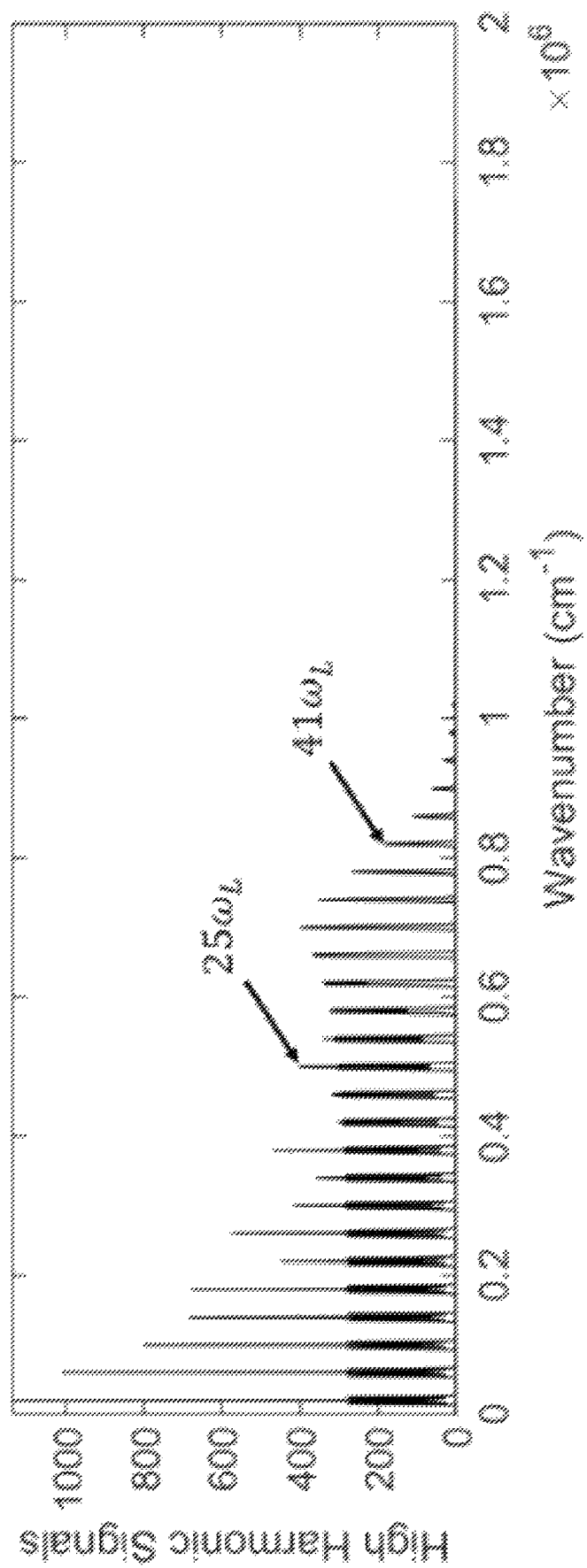
FIG. 14 illustrates Argon spectrum from ESPM at $I_0=2.6\times10^{16}$ W/m$^2$ with central wavelength at 500 nm with the calculated cutoff frequencies.

FIG. 14 shows the energy S(ω) example of HHG using FFT of E(t) for Argon with parameters above showing the cutoff. We have developed a simple maximum HHG cutoff frequency for material using electronic nonlinear index $n_2$ and physical properties and parameters of Laser intensity, angular frequency, and thickness of material z.

The cutoff frequency above contradicts the common HHG cutoff energy shown in the past approximately as $I_P+2U_P$ where, $I_p$ is the ionization energy and $U_p$ is ponderomotive energy $$\left(\text{varies as } \frac{I_L}{\omega_L^2}\right)$$

which is related to the kinetic energy of the electron. Extending the kinetic energy term given by Corkum and others, one finds that the $$2U_P \frac{\omega_L^2 z^2}{v_e^2}$$

($v_e$ is the velocity of the electron) is eliminating the $\omega_L^2$ in $U_P$ term. So, the classical theory does not have a $\lambda^2$ dependency unless the higher terms are considered. Also, in fact the semiclassical theory of Corkum [9] and the quantum mechanical theory of Lewenstein [10] do not take nonlinear optical response ($n_2$) of the media and the parameters of the carrier envelope phase of the electric field of the pulse into account.

It needs to be stated both instantaneous response to electronic part to optical carrier envelope phase and to the envelope of electric field response can occur to together with slow molecular repose in combination to generate X-rays and UV to RF regions where the nonlinear indices, $$n_2; n_4 = n_{electronic}(\text{Ultrafast}) + n_{molecular}(\text{fast/slow}) \quad (32)$$

For the microscope, we have found that Kerr SPM yields a most startling effect that the USC can extend from the D.C. region through entire electromagnetic spectra up to soft X-ray region for a higher ultrafast intensity in $CS_2$ and rare gases (Argon) because of the response of $n_2$ and $n_4$. The 532 nm produces longer SPM spectrum compared to 800 nm because of the interference from the negative $n_4$ at 800 nm decreases the spectrum. The materials mentioned above can also generate limited USC.

Figure 15:
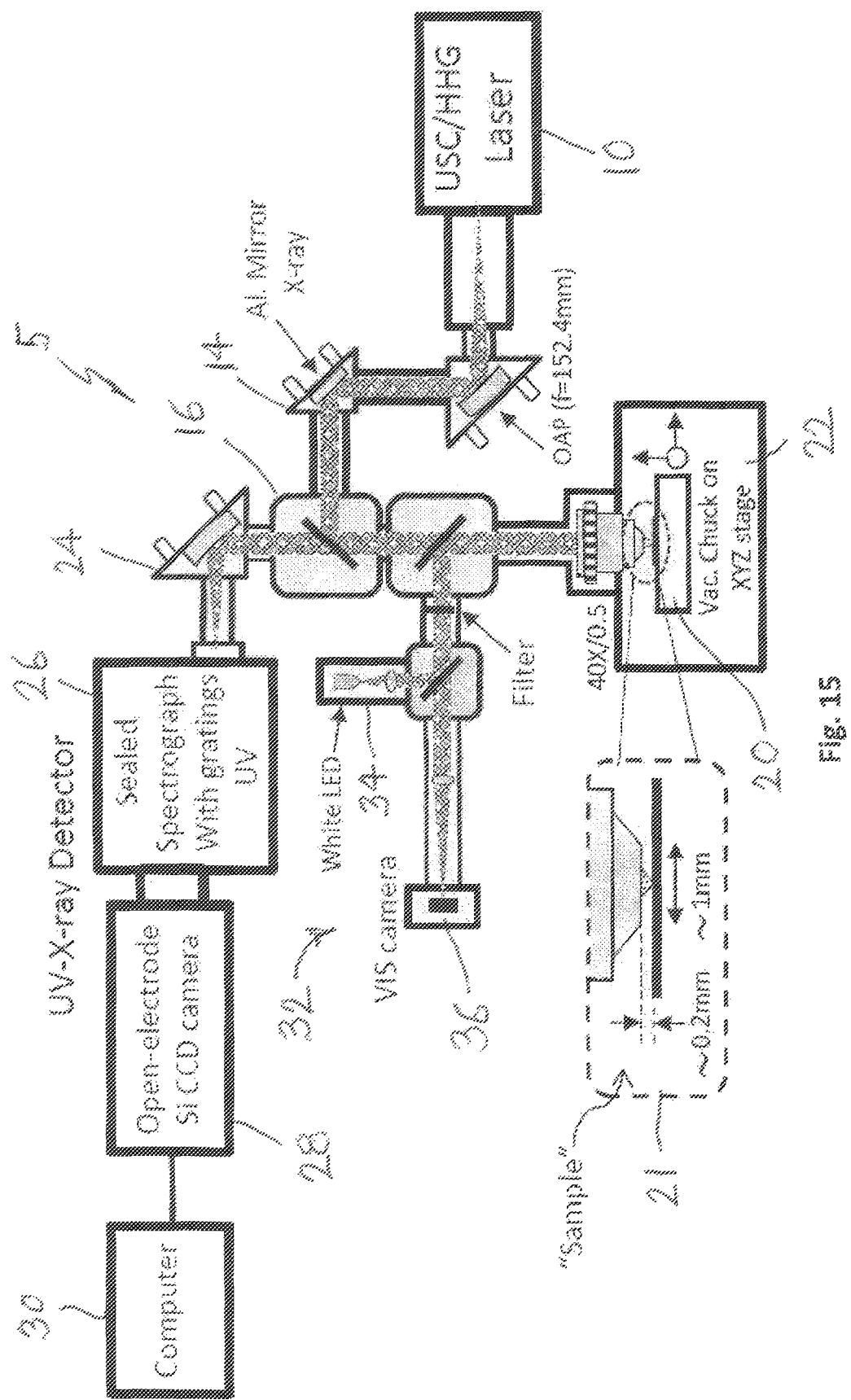
FIG. 15 illustrates the compact tabletop X-ray UV USC microscope.
Figure 16:
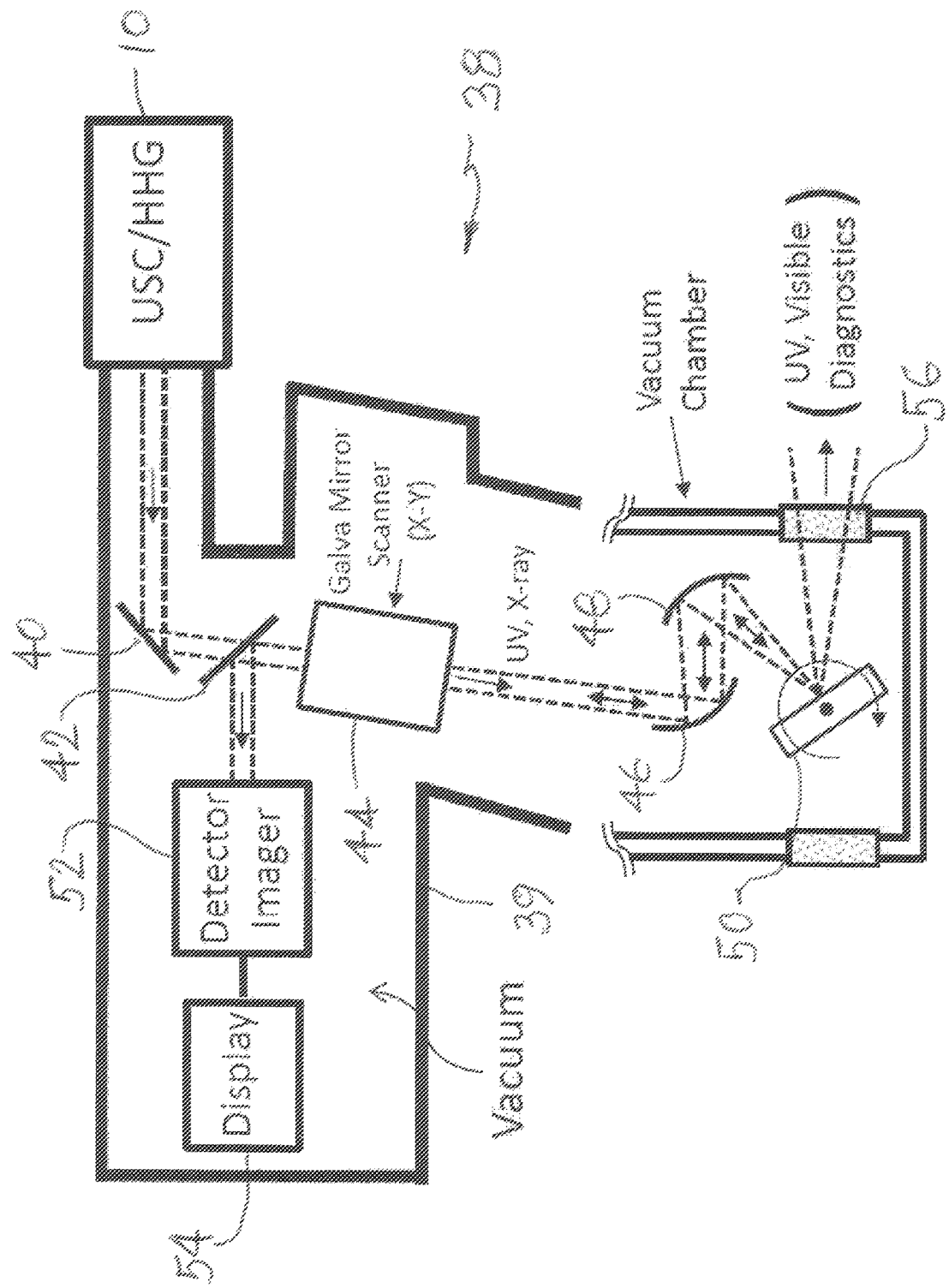
FIG. 16 illustrates the compact tabletop version of X-ray UV USC microscope in a vacuum chamber.

The ultra-supercontinuum source (USC) is taught for a tabletop microscope into UV, X-ray and gamma ray region see FIG. 15 and FIG. 16. The components to build this microscope are commercially available such as mirror scanners (Galvo), silicon photodetectors (https://optodiode.com/photodiodes-sxuv-detectors.html), X-ray gratings (https:www.ntt-at.com/product/xuv_transmission_grating/; https:// www.ntt-at.com/product/filter_euv/; https://www.shimadzu.com/opt/products/dif/o-k25cur0000006.zd0.html).

This UV X-ray microscope system can be used for applications to image genes, nucleus of cell components, nucleotides, and proteins to understand the most fundamental process in bio and nature by imaging on sub nm and nm scale.

The dispersion effects and the linear/non-linear absorption effects are not accounted for in the frequency spans and will modify the spectral extend. Any absorption from electronic states and/or bandgap will carve spectral holes in the SPM spectra or limit the spectra in the range of zero to X-rays. The ionization energy will limit the spectral range as well. The source of the USC can be numerous materials like $CS_2$, liquid/solid rare gases like Argon and Krypton, and Calcite. Absorption of the material will carve holes in the spectrum depending on the absorption spectrum of the materials [14]. USC spectrum can also be limited by the bandgap [15].

Stokes side of the USC for the IR, MIR, THz microscopes can be detected using photodiodes with amplifiers, grating, filters, and spectrometers. The similar arrangement is shown in FIG. 16.

Figure 17:
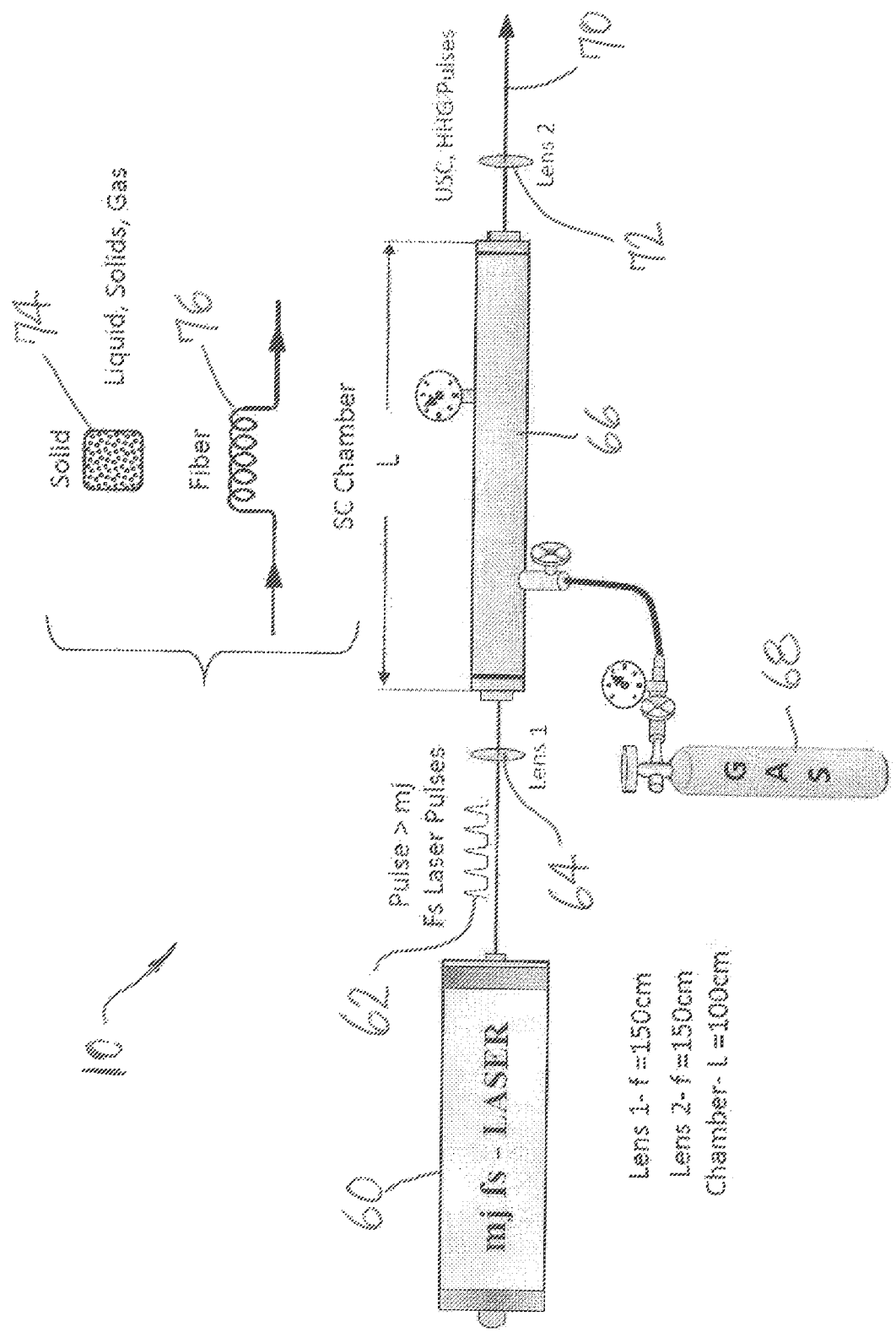
FIG. 17 illustrates the UV USC/HHG light source for FIGS. 15 and 16.
Figure 18:
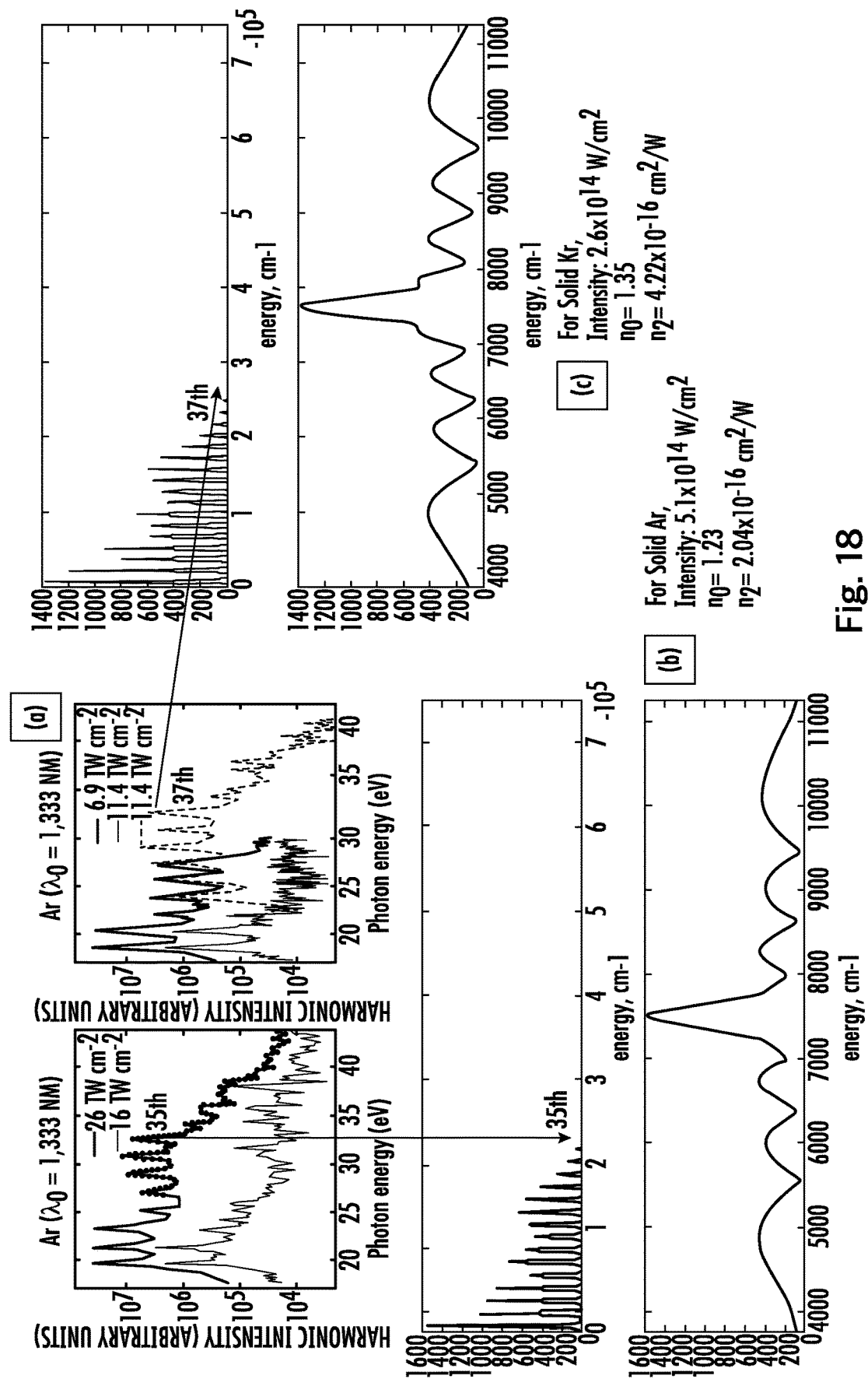
FIG. 18 illustrates the comparison between a) the experimental result of HHG in solid Ar and solid Kr and b) the theoretical prediction of HHG from the ESPM model in b) solid Ar and c) solid Kr after fitting the beam intensity.
Figure 19:
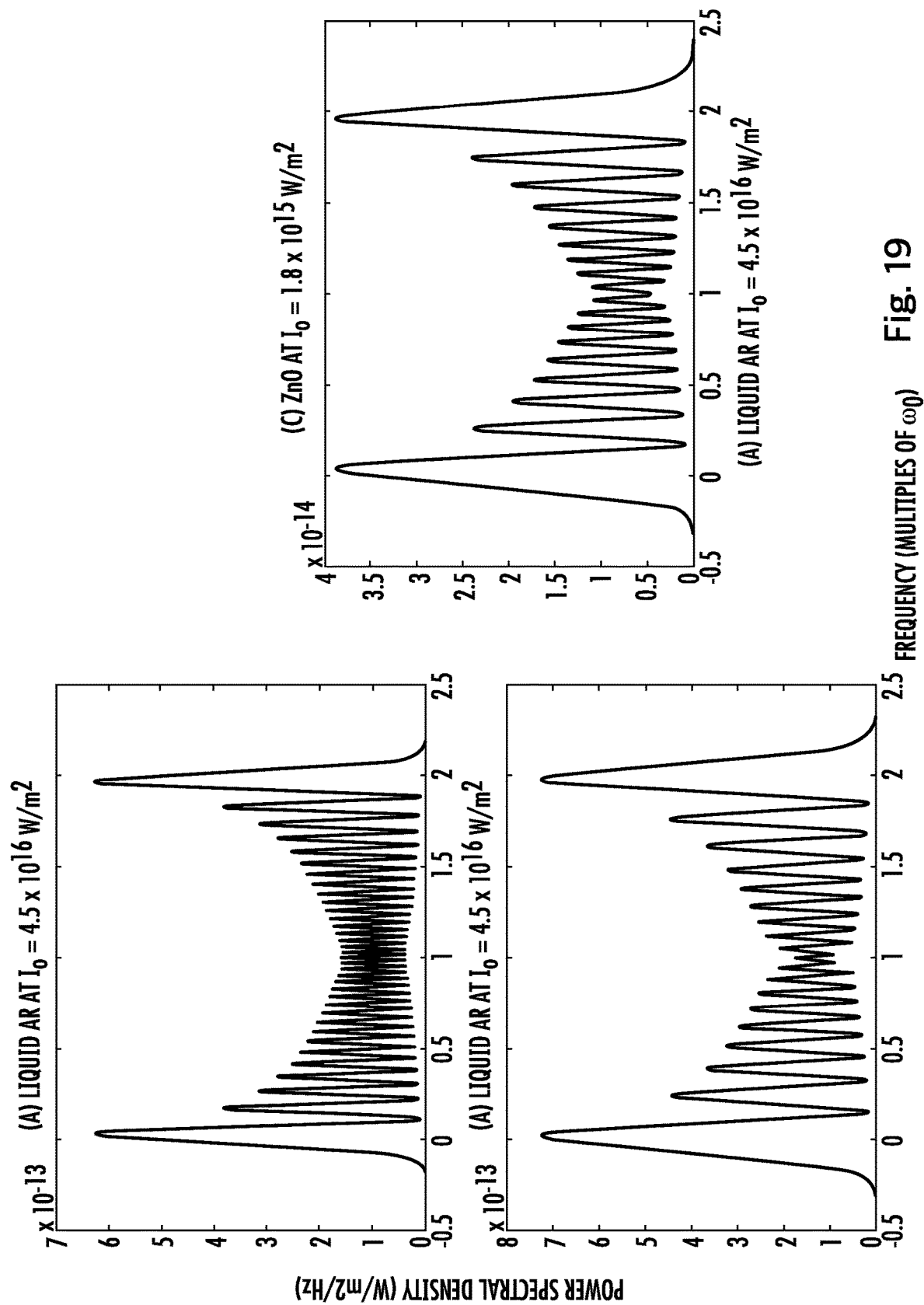
FIG. 19 illustrates SPM spectra comparison of A) liquid Argon at $I_0=4.5\times10^{16}$ W/m$^2$, B) Calcite at $I_0=3.4\times10^{16}$ W/m$^2$, and C) ZnO at $I_0=1.8\times10^{15}$ W/m$^2$.

Referring to FIG. 15 an apparatus 5 is shown utilizing the USC/HHG generator 10 in accordance with the invention shown in more detail in FIG. 17. The generator 10 generates a beam directed to a collimator 12. The collimated light is deflected by mirror 12 to a reflector 16 that directs the beam to a specimen 21. The specimen 21 is mounted on a XYZ stage 20 within a vacuum chamber 22. Light reflected from the sample is directed through the reflector 16 that also allows transmission of the beam, and that beam is converted from a collimated beam to a focused beam by element 24. The beam is then directed to a spectrograph 26 that forms part of a UV-X-ray detector the output of which is received by a Si CCD camera 28 that generates the image that can then be viewed on a computer screen 30. Optionally, the apparatus is provided with an alignment system 32 that includes a white LED 34 and a camera 36.

In FIG. 16, an apparatus 38 is shown that is encased within a vacuum chamber 39. The USC/HHG generator or source 10 that emanates beam deflected by mirror 40 through an optical component 42 to a galva mirror scanner 44. The beam, that may be collimated, is focused by mirrors 46, 48 onto sample 50 that is mounted for rotation as illustrated. The light reflected from the sample is re-directed through the galva mirror scanner 44 and reflected by the mirror 42 to detector imager 52 and can then be viewed on display 54. Optionally, the chamber 39 is provided with a window 56 through which the light can be transmitted for external additional processing such as by a spectrometer.

FIG. 17 shows in greater detail the generator 10 shown in FIGS. 15 and 16. The generator includes a mj fs laser 60 that produces high intensity mj fs pulses 62. The pulses are focused by lens 64 into one of a number of mediums as described above. In one possibility the pulses are directed into a SC chamber 66 supplied with a gas 68. The USC, HHG pulses 70 emanate through lens 72 and can be directed into an imaging system or apparatus.

The invention has numerous advantages and benefits not available with known methods and devices, including:

1. One can use this method to generate a portable tabletop UUV source.
2. One can use this method to generate a portable tabletop X-ray source.
3. The underlying processes has been taught from the slow non-electronic response to the fifth- and third-order susceptibilities and the fast instantaneous response from following carrier envelope phase under the influence of an extremely high-intensity femtosecond laser pulse to produce spectra broadening changes extending from extreme UV to DC.
4. One can use this method to generate a table gamma ray source.
5. One can use this method to generate a portable X-ray source.
6. One can use this method to generate a portable Gamma ray source.
7. One can use this method to generate a UV source.
8. It can be used for industrial engineering or inorganic materials imaging to detect its properties.
9. It can be applied for detecting biocompatible biomaterials properties in orthopedic field.
10. It can be applied for building into new generation of microscopy for extremely high-resolution imaging of biological specimen or inorganic materials.
11. It can be applied for building into new generation of microscopy for extremely high resolution (nanometer scale) imaging of DNA structures and dynamics in vitro or in vivo.
12. It can be applied for building into new generation of microscopy for extremely high resolution (nanometer scale) imaging of gene structures and dynamics in vitro or in vivo,
13. It can be applied for building into new generation of microscopy for extremely high resolution (nanometer scale) imaging of mitochondrial structural and functional dynamics in vitro, ex vivo, or in vivo, such as inner membrane and outer membrane structural and its functional dynamics which related to environmental stress, aging, inflammation and diseases such as cancer, metabolic syndrome, alzheimer's, dementia, or other neurodegenerative diseases.
14. It can be applied for building into new generation of microscopy for extremely high resolution (nanometer scale) imaging of Endoplasmic reticulum (ER) structures and functional dynamics in vitro, ex vivo, or in vivo, such as ER membrane's structural and functional dynamics which related to environmental stress, aging, inflammation and diseases such as cancer, metabolic syndrome, alzheimer's, dementia, or other neurodegenerative diseases.
15. It can be applied for building into new generation of microscopy for extremely high resolution (nanometer scale) imaging of exosomes' structures and functional dynamics in vitro, ex vivo, or in vivo, such as exosomes' structural and functional dynamics which related to environmental stress, aging, inflammation and diseases such as cancer, metabolic syndrome, alzheimer's, dementia, or other neurodegenerative diseases.
16. It can be applied for building into new generation of microscopy for extremely high resolution (nanometer scale) imaging of nucleus' membrane structures and functional dynamics in vitro, ex vivo, or in vivo, such as nucleus' membrane's structural and functional dynamics which related to environmental stress, aging, inflammation, and diseases such as cancer, metabolic syndrome, alzheimer's, dementia, or other neurodegenerative diseases.
17. It can be applied for building into new generation of microscopy for extremely high resolution (nanometer scale) imaging of vesicles' structures and functional dynamics in vitro, ex vivo, or in vivo, such as vesicles' membrane's structural and functional dynamics which related to environmental stress, aging, inflammation, and diseases such as cancer, metabolic syndrome, alzheimer's, dementia, or other neurodegenerative diseases.
18. It can be applied for building into new generation of microscopy for extremely high resolution (nanometer scale) imaging of RNA structures and functional dynamics in vitro, ex vivo, or in vivo, such as RNA structural and functional dynamics which related to environmental stress, aging, inflammation, and diseases such as cancer, metabolic syndrome, alzheimer's, dementia, or other neurodegenerative diseases.
19. It can be applied for building into new generation of microscopy for extremely high resolution (nanometer scale) imaging of nanocarrier's structures and functional dynamics in vitro, ex vivo, or in vivo, such as nanocarrier's structural and functional dynamics which related to drug delivery field.
20. It can be applied for building into new generation of microscopy for extremely high resolution (nanometer scale) imaging of drug molecules' structures and functional dynamics in vitro, ex vivo, or in vivo, such as molecules' structural and functional dynamics which related to drug design and pharmaceutical field.
21. It can be applied for building into new generation of microscopy for extremely high resolution (nanometer scale) imaging of skin care products' molecule structures and functional dynamics in vitro, ex vivo, or in vivo, such as molecules' structural and functional dynamics which related to skin care and antiaging field.
22. It can be applied for building into new generation of microscopy for extremely high resolution (nanometer scale) imaging of nano particle structures and functional dynamics, such as molecules' structural and functional dynamics which related nano-engineering research.
23. It can be applied for studying and measuring structural and functional dynamics of material designed for batteries.
24. It can be applied for studying and measuring structural and functional dynamics of nanomaterial designed for cosmetics.
25. This can be applied for higher resolution biomedical imaging for rapid diagnosis of bone health or tissue health.
26. This can be applied for oral or dental health diagnosis and evaluation.
27. The Stokes MIR, IR and THz parts of the spectrum can be used to image the vibrational interaction in bio and chemical interaction as a part of the microscope with micron size resolution.

The followings are the claims on the teachings presented above on the spectral broadening, Higher Harmonic Generation, and attosecond pulse production in various states of matter from n(t) caused by extreme femtosecond laser pulses.

The invention claimed is:

1. Method of generating broad spectra ultra-high frequency spread spanning from Extreme UV (EUV) to far infrared (FIR) comprising the step of introducing high intensity I pump laser pulses 25 fs to 200 fs from 100 µJ to 50 mJ into a medium having third and fifth order components of electric susceptibility $\chi^3$ and $\chi^5$, respectively, and an average Kerr nonlinear index of refraction $$\leq n(t) \geq = n_0 + n_2 I + n_4 I^2,$$

said pulses including ps varying approximation (SVA) following the envelope of a light field and $n_2 I$ is a first order non-linear Kerr index of refraction related to $\chi^3$ and $n_4 I^2$ is a second order non-linear Kerr index of refraction related to $\chi^5$ at laser pulse within the range of $10^{14} \sim 10^{20}$ W/m², where $n_2$ is a non-linear Kerr index of refraction representing molecular movements that arises from ps response $\chi^3$ and $n_4$ is a non-linear Kerr index of refraction representing electric field that arises from $\chi^5$ to produce ultra-supercontinuum (USC) light.

2. The method of claim 1, wherein the laser pulses are in the spectral region of 500 nm to 2200 nm.

3. The method of claim 1, wherein the laser can generate pulses 5 mJ, 100 fs at 517 nm, 532 nm, 800 nm, 1035 nm, and 1064 nm pulse focus with lens to spot into condensed media containing nonlinear media.

4. The method of claim 1, wherein the laser can generate pulses 5 mJ, 100 fs at 517 nm, 532 nm, 800 nm, 1035 nm, and 1064 nm pulse focus with lens to spot into a hollow optical fiber containing nonlinear media.

5. The method of claim 3, wherein condensed media can be liquids (Argon, Krypton, Nitrogen, $CS_2$) placed in hollow fiber, glass, or crystal of length 1 cm to 20 cm long.

6. The method of claim 1, wherein the nonlinear n2 is positive and n4 can be positive or negative depending on pump wavelength.

7. The method of claim 1, wherein the spectral range extends from Ultra SC from DC to UV, from THz to UV, SWIR to visible to UV to microscopes.

8. The method of claim 4, wherein the materials used for an envelope response are the liquids such as $CS_2$ and rare gas liquids including liquid $N_2$, liquid Argon and liquid Krypton and condensed matter such as LBG glass, and calcite.

9. The method of claim 4, wherein The materials used for an electronic response are the rare gases like Argon, Krypton and condensed matter like BK-7 glass.

10. The method of claim 1, wherein a Kerr mode locking from a Kerr medium can generate attosecond pulses from these deltas like HHG peak which will be locked in phase with the aperture or beam confinement to give attosecond pulse from a transform-limited of Gaussian relation:

$$\tau_p = \frac{0.4}{N(2\omega_0)},$$

wherein N=31 coupled modes driven by the intense pump beam will have the Kerr mode-locking from $n_2$ giving $\tau_p$ of 20 attoseconds.

11. Apparatus for generating broad spectra ultra-high frequency spread spanning from Extreme UV (EUV) to far infrared (FIR) comprising means for introducing high intensity I pump laser pulses 25 fs to 200 fs from 100 µJ to 50 mJ into a medium having third and fifth order components of electric susceptibility $\chi^3$ and $\chi^5$, respectively, and an average Kerr nonlinear index of refraction $$\leq n(t) \geq = n_0 + n_2 I + n_4 I^2,$$

said pulses including ps varying approximation (SVA) following the envelope of a light field and $n_2 I$ is a first order non-linear Kerr index of refraction related to $\chi^3$ and $n_4 I^2$ is a second order non-linear Kerr index of refraction related to $\chi^5$ at laser pulse within the range of $10^{14} \sim 10^{20}$ W/m², where $n_2$ is a non-linear Kerr index of refraction representing molecular movements that arises from ps response $\chi^3$ and $n_4$ is a non-linear Kerr index of refraction representing electric field that arises from $\chi^5$ to produce ultra-supercontinuum (USC) light; and means for maintaining the medium in a vacuum.

12. Imaging apparatus for imaging a sample with broad spectra ultra-high frequency spread spanning from Extreme UV (EUV) to far infrared (FIR) comprising means for introducing high intensity I pump laser pulses 25 fs to 200 fs from 100μJ to 50 mJ into a medium having third and fifth order components of electric susceptibility $\chi^3$ and $\chi^5$, respectively, and an average Kerr nonlinear index of refraction $$\leq n(t) \geq = n_0 + n_2 I + n_4 I^2,$$

said pulses including varying approximation (SVA) following the envelope of a light field and $n_2 I$ is a first order non-linear Kerr index of refraction related to $\chi^3$ and $n_4 I^2$ is a second order non-linear Kerr index of refraction related to $\chi^5$ at laser pulse within the range of $10^{14} \sim 10^{20}$ W/m$^2$, where $n_2$ is a non-linear Kerr index of refraction representing molecular movements that arises from ps response $\chi^3$ and $n_4$ is a non-linear Kerr index of refraction representing electric field that arises from $\chi^5$ to produce ultra-supercontinuum (USC) light; first optics for directing the USC light onto a specimen to be imaged; second optics for directing the light emanating from the sample to an image detector; and display means for displaying the image.

13. The imaging apparatus of claim 12, wherein said first optics includes a collimator to collimate the light directed at the sample.

14. The imaging apparatus of claim 12, wherein said second optics includes a focusing element to focus collimated lights emanating from the sample; and further comprising a spectrograph with gratings.

15. The imaging apparatus of claim 12, wherein said display means comprises an open electrode Si CCD cameral; and a computer for displaying the image detected by said CCD camera.

16. The imaging apparatus of claim 12, wherein said sample is maintained with a vacuum chamber.

17. The imaging apparatus of claim 12, wherein said first and second optics include a galva mirror scanner.

18. The imaging apparatus of claim 12, wherein said first optics comprises means for converting the collimated USC light to a focused beam directed at the specimen.

19. The imaging apparatus of claim 12, wherein said sample is mounted for rotation.

20. The imaging apparatus of claim 19, wherein said sample is mounted with a vacuum chamber; and further comprising a window proximate to said rotatable sample for transmitting light reflected from the sample to a point outside said vacuum chamber for visible diagnostics.

21. The method of claim 1, wherein the ps non-electronic response to the fifth- and third-order susceptibilities and an instantaneous response from following carrier envelope phase is under the influence of an extremely high-intensity femtosecond laser pulse to produce spectra broadening changes extending from extreme UV to DC.

22. The method of claim 1, wherein the non-linear Kerr index of refraction n2 is instantaneous with response to a phase and an envelope at extreme intensities to generate high harmonic generation (HHG) of the laser frequency.

* * * * *